United States Patent
Shiba et al.

(10) Patent No.: US 12,078,648 B2
(45) Date of Patent: Sep. 3, 2024

(54) SAMPLE MEASUREMENT DEVICE AND SAMPLE MEASUREMENT METHOD

(71) Applicant: SYSMEX CORPORATION, Kobe (JP)

(72) Inventors: Masaki Shiba, Kobe (JP); Hiroki Kotake, Kobe (JP); Akihito Kato, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 685 days.

(21) Appl. No.: 16/824,198

(22) Filed: Mar. 19, 2020

(65) Prior Publication Data
US 2020/0309801 A1  Oct. 1, 2020

(30) Foreign Application Priority Data

Mar. 27, 2019  (JP) ................. 2019-061846

(51) Int. Cl.
*G01N 35/00* (2006.01)
*G01N 33/49* (2006.01)
(Continued)

(52) U.S. Cl.
CPC ... *G01N 35/00871* (2013.01); *G01N 33/4905* (2013.01); *G01N 35/025* (2013.01);
(Continued)

(58) Field of Classification Search
CPC ......... G01N 35/00871; G01N 33/4905; G01N 35/025; G01N 35/1065; G01N 35/1081;
(Continued)

(56) References Cited

U.S. PATENT DOCUMENTS

2004/0258566 A1* 12/2004 James Smith ......... G01N 35/04
422/65
2008/0318323 A1* 12/2008 Shintani ............... B01L 3/5082
422/63
(Continued)

FOREIGN PATENT DOCUMENTS

| CN | 103675304 A | 3/2014 |
|---|---|---|
| CN | 103675309 A | 3/2014 |

(Continued)

OTHER PUBLICATIONS

Extended European search report issued on Aug. 25, 2020 in a counterpart European patent application No. 20162057.2.
(Continued)

*Primary Examiner* — Jill A Warden
*Assistant Examiner* — John McGuirk
(74) *Attorney, Agent, or Firm* — Crowell & Moring LLP

(57) ABSTRACT

Disclosed is a sample measurement device comprising a first processing unit that performs a first measurement on a sample contained in a first container in a first cycle; a second processing unit that performs a second measurement on a sample contained in a second container in a second cycle different from the first cycle; and a relay section which is disposed between the first processing unit and the second processing unit and in which the second container is positioned, wherein the first processing unit performs a transferring operation of transferring the second container to the relay section, and the second processing unit performs a receiving operation of receiving the second container that has been transferred to the relay section from the relay section.

10 Claims, 14 Drawing Sheets

(51) Int. Cl.
*G01N 35/02* (2006.01)
*G01N 35/10* (2006.01)

(52) U.S. Cl.
CPC ..... *G01N 35/1065* (2013.01); *G01N 35/1081* (2013.01); *G01N 2035/00346* (2013.01)

(58) Field of Classification Search
CPC .......... G01N 2035/00346; G01N 2035/00326; G01N 35/04; G01N 2035/0453; G01N 2035/0462; G01N 2035/0465; G01N 21/31; G01N 33/50; G01N 33/86; G01N 35/0092

See application file for complete search history.

(56) References Cited

U.S. PATENT DOCUMENTS

| | | | |
|---|---|---|---|
| 2010/0248293 A1* | 9/2010 | Kuwano | G01N 35/0092 435/287.1 |
| 2012/0171078 A1* | 7/2012 | Kaneko | G01N 35/04 422/65 |
| 2019/0265261 A1 | 8/2019 | Yamaguchi et al. | |
| 2019/0339295 A1* | 11/2019 | Makino | G01N 35/04 |

FOREIGN PATENT DOCUMENTS

| | | |
|---|---|---|
| CN | 107271709 A | 10/2017 |
| CN | 107422137 A | 12/2017 |
| CN | 107850612 A | 3/2018 |
| CN | 109975565 A | 7/2019 |
| EP | 1870713 A1 | 12/2007 |
| EP | 2485057 A1 | 8/2012 |
| EP | 3086123 A1 | 10/2016 |
| EP | 3349013 A1 | 7/2018 |
| EP | 3508858 A1 | 7/2019 |
| JP | 2001-013151 A | 1/2001 |
| JP | 2009210304 A * | 9/2009 ............ G01N 35/04 |
| JP | 2011-017716 A | 1/2011 |
| JP | 2015-190787 A | 11/2015 |
| JP | 2017-096894 A | 6/2017 |
| WO | WO2011/093442 | 8/2011 |
| WO | WO2013/187210 | 12/2013 |
| WO | 2018055885 A1 | 3/2018 |

OTHER PUBLICATIONS

Japanese Office Action with English Translation, issued on Oct. 25, 2022, pp. 1-10, in a counterpart Japanese patent application No. 2019-061846.

Decision of Refusal with English Translation, dated Feb. 28, 2023, pp. 1-6, issued in Japanese patent application No. 2019-061846, Japan Patent Office, Chiyoda Tokyo, Japan.

Chinese Office Action issued on Oct. 27, 2023 in a counterpart Chinese patent application No. 202010198044.5, 21 pages.

Chinese Office Action issued on May 11, 2024 in a counterpart Chinese patent application No. 202010198044.5, 25 pages.

* cited by examiner

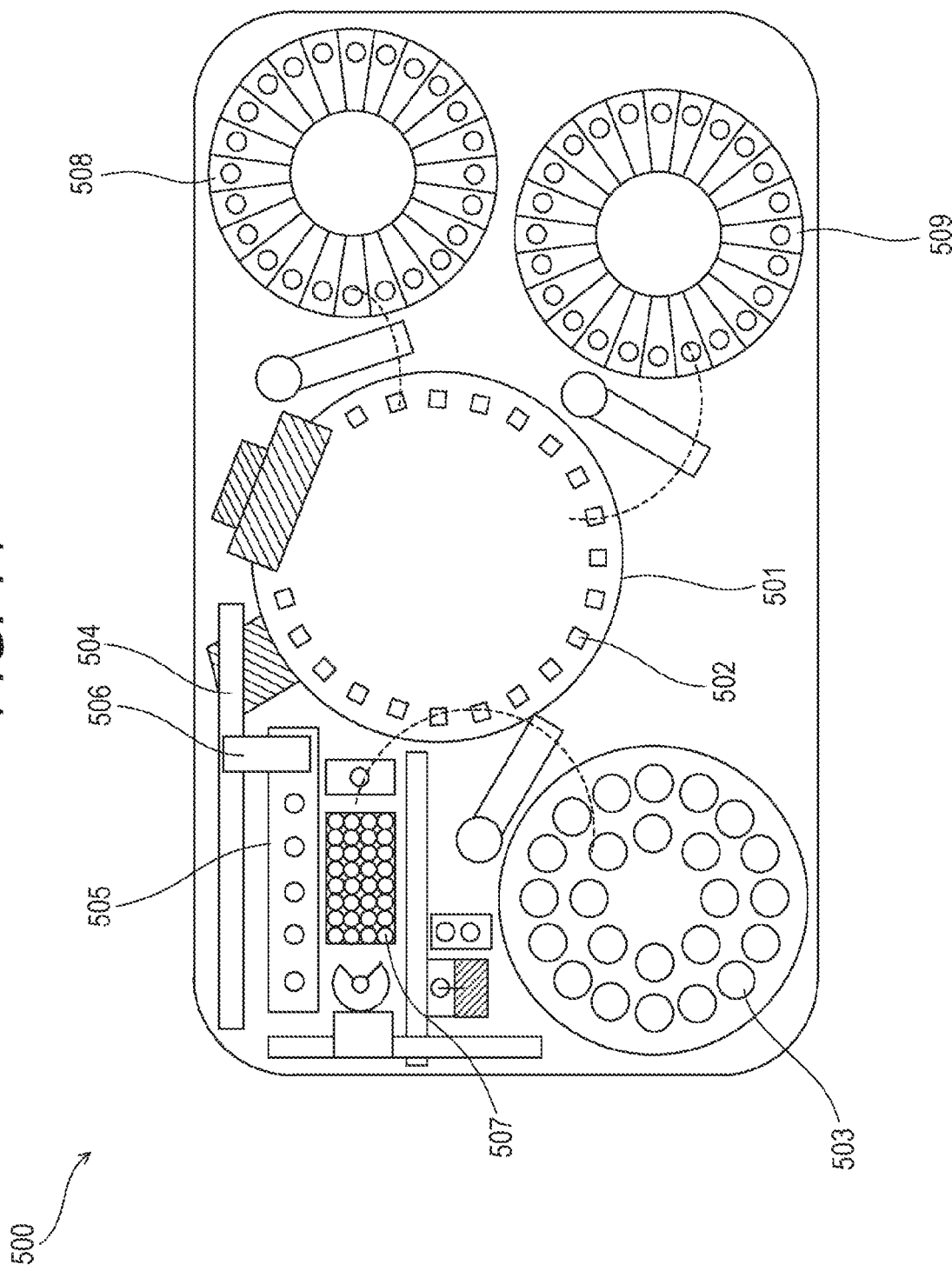

SAMPLE MEASUREMENT DEVICE AND SAMPLE MEASUREMENT METHOD

RELATED APPLICATIONS

This application claims priority to Japanese Patent Application No. 2019-061846, filed on Mar. 27, 2019, the entire content of which is incorporated herein by reference.

BACKGROUND OF THE INVENTION

1. Field of the Invention

The present invention relates to a sample measurement device and a sample measurement method for measuring a sample.

2. Description of the Related Art

Conventionally, a device for performing both biochemical measurement and blood coagulation measurement has been known, for example, as a device for analyzing an amount of components contained in a sample such as blood or urine. In an automatic analyzer 500 disclosed in US 2015104351, as shown in FIG. 14, when a biochemical measurement is performed, a sample is dispensed from a sample container 503 to a reaction cell 502 housed in a rotatable reaction disk 501, and then, a predetermined amount of reagent is dispensed from a first reagent disk 508 to the reaction cell 502, and the sample and the reagent are stirred. The absorbance of the sample and the reagent in the reaction cell 502 is measured each time the sample and the reagent cross in front of a photometer 504 during the rotating operation of the reaction disk 501.

When a blood coagulation measurement is performed, a sample is dispensed from the sample container 503 to a reaction container 507, and the sample is heated to 37° C. in the reaction container 507. Meanwhile, a reagent for measuring blood coagulation time is dispensed from a second reagent disk 509 into the vacant reaction cell 502 by rotating the reaction disk 501, and the temperature of the reagent is raised. When the temperature increase of the reagent for measuring the blood coagulation time is completed, the reaction cell 502 is located at a blood coagulation reagent suction position, and the reagent is sucked by a dispensing mechanism 506 and discharged to the reaction container 507. At this time, the sample and the reagent are stirred by a spurt of the reagent being discharged, and the measurement of the blood coagulation time starts.

When the biochemical measurement and the blood coagulation measurement are performed, if T1 is a time required to perform one cycle of the blood coagulation measurement and T2 is a time required to perform one cycle of the biochemical analysis, the automatic analyzer 500 is controlled such that T1 is a multiple of n (n is a natural number) of T2.

Therefore, when n is 2 or more, for example, the timing for starting the blood coagulation measurement always overlaps with the timing for starting the biochemical analysis. Thus, it is possible to perform the blood coagulation measurement and the biochemical measurement in parallel.

In US 2015104351, in order to perform both the biochemical measurement and the blood coagulation measurement in the automatic analyzer 500, control to align the timings at which the two measurements are started, that is, control to synchronize the two measurements, is performed. However, the control to synchronize two measurements is complex. Meanwhile, if the synchronization timing is slightly shifted, there is a possibility that both measurements will not proceed as expected and will be delayed.

SUMMARY OF THE INVENTION

A first aspect of the present invention relates to a sample measurement device for measuring a sample. Referring to FIG. 1, a sample measurement device (100) according to the present aspect includes a first processing unit (61) that performs a first measurement on a sample contained in a first container (21) in a first cycle; a second processing unit (62) that performs a second measurement on a sample contained in a second container (21) in a second cycle different from the first cycle; and a relay section (201) which is disposed between the first processing unit (61) and the second processing unit (62) and in which the second container (21) is positioned. The first processing unit (61) performs a transferring operation of transferring the second container (21) to the relay section (201), and the second processing unit (62) performs a receiving operation of receiving the second container (21), from the relay section (201), that has been transferred to the relay section (201).

In order to analyze the disease of a subject in more detail, the results of two measurements (two different types of measurements) may be combined. For example, disseminated intravascular coagulation (DIC) can be diagnosed by combining a measurement result regarding a blood coagulation test and a measurement result regarding an immunological test. Specifically, the diagnosis of DIC is made on the basis of the coagulation time obtained from the measurement result regarding the blood coagulation test, and PIC, TAT, etc., obtained from the measurement result regarding the immunological test. As described above, a measurement related to the blood coagulation test is performed as the first measurement, a measurement related to the immunological test is performed as the second measurement, and the measurement results of these measurements are combined. Thus, an appropriate measurement can be performed.

In this regard, according to the sample measurement device of the present aspect, the first measurement and the second measurement having different measurement cycles are performed by a single device. The first processing unit transfers the second container containing a sample to the relay section at an arbitrary timing, and the second processing unit receives the second container from the relay section at an arbitrary timing. Accordingly, even if the measurement cycles are different between the first processing unit and the second processing unit, the first processing unit and the second processing unit can transfer the second container to the relay section or receive the second container from the relay section at a preferable timing for the respective processing units without being affected by each other's operating statuses. Therefore, the first measurement and the second measurement can be performed smoothly and quickly without performing complicated control.

The first cycle and the second cycle described above indicate the time required for measuring the sample. The time required for measuring the sample is the total time required for each step included in one measurement. For example, if the first measurement includes a step of dispensing a reagent to the sample, a step of stirring the sample, a step of heating the sample, a step of centrifugation, and a step of performing a measurement for a predetermined measurement item, the first cycle in the first measurement indicates a time required to complete these five steps.

Referring to FIG. 3, the sample measurement device (100) according to the present aspect may be configured such that the relay section (201) includes a detector (80, 81) for detecting the second container (21).

According to the sample measurement device of the present aspect, the first processing unit can position the second container in the relay section, and the second processing unit can receive the second container from the relay section, after the presence or absence of the second container in the relay section is accurately recognized.

Referring to FIGS. 9B and 9C, the sample measurement device (100) according to the present aspect may further include a management device (64) capable of communicating with the first processing unit (61) and the second processing unit (62), and may be configured such that the management device (64) transmits, to the first processing unit (61), a first signal indicating that the second container (21) is transferable to the relay section (201) on the basis of the detection result of the detector (80, 81), and the first processing unit (61) executes the transferring operation when receiving the first signal.

According to the sample measurement device of the present aspect, the management device transmits the first signal to the first processing unit on the basis of the detection result of the detector, that is, the detection result of whether the second container is positioned in the relay section. The first processing unit receiving the first signal performs the transferring operation of transferring the second container to the relay section. Therefore, the first processing unit can transfer the second container to the relay section at an arbitrary timing regardless of the operating status of the second processing unit.

Referring to FIGS. 9A and 9C, the sample measurement device (100) according to the present aspect may be configured such that, when the second container (21) is detected in the relay section (201), the second processing unit (62) executes the receiving operation and transmits, to the management device (64), a second signal indicating that the second processing unit receives the second container (21) that has been positioned in the relay section (201), and the management device (64) transmits the first signal to the first processing unit (61) when receiving the second signal.

According to the sample measurement device of the present aspect, the second processing unit performs the receiving operation of receiving the second container from the relay section after it is detected that the second container is positioned in the relay section. Therefore, the second processing unit can receive the second container from the relay section at an arbitrary timing regardless of the operating status of the first processing unit.

Referring to FIGS. 9A to 9C, in the sample measurement device (100) according to the present aspect, the first processing unit (61) includes a first transfer section (142) that transfers the second container (21) to the relay section (201), and a first controller (61a) that controls the first transfer section (142). The second processing unit (62) includes a second transfer section (202) that transfers the second container (21) from the relay section (201) to a predetermined position, and a second controller (62a) that controls the second transfer section (202). The sample measurement device (100) may be configured such that when the second container (21) is detected in the relay section (201), the second controller (62a) controls the second transfer section (202) such that the second container (21) is transferred from the relay section (201), and transmits the second signal to the management device (64); the management device (64) transmits the first signal to the first controller (61a) when receiving the second signal from the second controller (62a); and the first controller (61a) controls the first transfer section (142) such that the second container (21) is transferred to the relay section (201) when receiving the first signal from the management device (64).

In the sample measurement device according to the present aspect, the fact that the second signal is transmitted from the second controller to the management device means that the second container can be newly positioned in the relay section. Therefore, when the first signal is transmitted from the management device to the first controller, the first controller transfers the second container to the relay section. In this way, the first processing unit and the second processing unit can access the relay section, and receive and transfer the second container containing the sample without being affected by each other's operating statuses.

Referring to FIG. 13, the sample measurement device (100) according to the present aspect may be configured such that the relay section (201) includes a plurality of holding holes (201a) for holding a plurality of second containers (21).

According to the sample measurement device of the present aspect, the second containers can be respectively positioned in the plurality of holding holes provided in the relay section. Therefore, even when the second processing unit is performing the second measurement, and has not yet received the second container from the relay section, for example, the first processing unit can position the second container to the vacant holding hole of the relay section. Accordingly, the first processing unit can transfer the second container to the relay section at an arbitrary timing of the first processing unit without being affected by the operating status of the second processing unit.

Referring to FIG. 1, the sample measurement device (100) according to the present aspect may be configured such that the second processing unit (62) includes a holding section (210) that holds the second container (21) transferred from the relay section (201).

For example, when the second containers are held in the respective holding holes of the relay section, the first processing unit cannot transfer the second container to the relay section until there is a vacant holding hole in the relay section. In this regard, according to the sample measurement device of the present aspect, the second container can be stored in the holding section. Therefore, the second processing unit can transfer the second container positioned in the relay section to the holding section at an arbitrary timing, and can prepare a vacant holding hole in the relay section as quickly as possible. Accordingly, the waiting time of the first processing unit until the holding hole of the relay section becomes available is reduced. Thus, the first processing unit can quickly transfer the second container to the relay section.

Further, since the first processing unit can quickly transfer the second container to the relay section, the first processing unit can quickly finish the processing for the second container. Therefore, the first processing unit can quickly start the first measurement on the sample.

Referring to FIGS. 5A and 5B, in the sample measurement device (100) according to the present aspect, the first measurement is a measurement related to a blood coagulation test, and the second measurement is a measurement related to an immunological test.

Referring to FIG. 1, the sample measurement device (100) according to the present aspect may be configured such that the sample to be contained in the first container (21) is dispensed into the first container (21) from a sample container (10) containing the sample is contained, the sample to be contained in the second container (21) is dispensed from the sample container (10) from which the sample has been dispensed, and the second container (21) is transferred to the second processing unit (62) from the first processing unit (61) via the relay section (201).

According to the sample measurement device of the present aspect, the first processing unit and the second processing unit can perform the first measurement and the second measurement on the same sample (same type of the sample collected from the same subject). Therefore, when the sample measurement device according to the present aspect is used for, for example, a disease test, a lot of information can be obtained for the same sample, and by combining the obtained information pieces, a highly reliable test result can be obtained.

Referring to FIG. 1, the sample measurement device (100) according to the present aspect may include a dispensing section (30) for dispensing a sample from the sample container (10) to the first container (21) and the second container (21).

According to the sample measurement device of the present aspect, the sample used in the first processing unit and the second processing unit can be dispensed from the sample container using one dispensing section. Therefore, an increase in size of the device can be prevented.

The sample measurement device (100) according to the present aspect may be configured such that the sample to be contained in the first container (21) is dispensed into the first container (21) from a sample container (10) containing the sample, the sample to be contained in the second container (21) is dispensed from the first container (21) into the second container (21) in the first processing unit (61), and the second container (21) into which the sample has been dispensed is transferred to the second processing unit (62) via the relay section (201).

According to the sample measurement device of the present aspect, the sample contained in the first container and the sample contained in the second container are given from the sample contained in the same sample container in two dispensations. Therefore, when the sample is dispensed into the second container after the dispensation of the sample from the sample container into the first container, an occurrence of contamination can be reduced.

Referring to FIG. 2, the sample measurement device (100) according to the present aspect may further include a transport unit (63) for transporting a sample rack (101) holding a plurality of sample containers (10), and may be configured such that the plurality of sample containers (10) held in the sample rack (101) is transported to the dispensing position of the first processing unit (61) by the transport unit (63), and the sample dispensed into the first container (21) and the second container (21) in the first processing unit (61) from each of the plurality of sample containers (10) at the dispensing position is measured by the first processing unit (61) and the second processing unit (62).

According to the sample measurement device of the present aspect, the sample is dispensed at one location in the first processing unit, so that the configuration of the device can be simplified.

A second aspect of the present invention relates to a sample measurement method for measuring a sample. Referring to FIGS. 9A to 9C, a sample measurement method according to the present aspect includes performing a first measurement on a sample contained in the first container (21) in a first cycle in the first processing unit (61); transferring the second container (21) containing a sample to the second processing unit (62) from the first processing unit (61); and performing a second measurement on the sample contained in the second container (21) in a second cycle different from the first cycle in the second processing unit (62).

The sample measurement method according to the present aspect can provide the same effects as those in the first embodiment.

Referring to FIGS. 9B and 9C, the sample measurement method according to the present aspect may be configured to transfer the second container (21) from the first processing unit (61) to the second processing unit (62) via the relay section (201) which is disposed between the first processing unit (61) and the second processing unit (62) and in which the second container (21) is positioned.

Referring to FIG. 9C, the sample measurement method according to the present aspect may be configured to transmit, to the first processing unit (61) from the management device (64) capable of communicating with the first processing unit (61) and the second processing unit (62), a first signal indicating that the second container (21) can be transferred to the relay section (201), and to transfer the second container (21) to the relay section (201) from the first processing unit (61) when the first processing unit (61) receives the first signal.

Referring to FIG. 9C, the sample measurement method according to present aspect may be configured to transmit, to the management device (64) from the second processing unit (62), a second signal indicating that the second processing unit (62) receives the second container (21) that has been positioned in the relay section (201), and to transmit the first signal to the first processing unit (61) from the management device (64) when the management device (64) receives the second signal.

Referring to FIG. 9C, the sample measurement method according to the present aspect may be configured to, when the second container (21) is positioned in the relay section (201), transfer the second container (21) from the relay section (201) to the second processing unit (62), transmit the second signal to the management device (64) from the second processing unit (62), transmit the first signal from the management device (64) to the first processing unit (61) when the management device (64) receives the second signal, and transfer the second container (21) to the relay section (201) from the first processing unit (61) when the first processing unit (61) receives the first signal.

Referring to FIG. 8, the sample measurement method according to the present aspect may be configured to dispense the sample into the first container (21) from the sample container (10) in the first processing unit (61), dispense the sample into the second container (21) from the sample container (10) in the first processing unit (61), and transfer the second container (21) to the second processing unit (62) from the first processing unit (61).

Referring to FIGS. 5A and 5B, in the sample measurement method according to the present aspect, the first measurement may be a measurement related to a blood coagulation test, and the second measurement may be a measurement related to an immunological test.

The present invention can provide a sample measurement device capable of performing two measurements with one device without requiring complicated control, and a sample measurement method using the sample measurement device.

The scope of the present invention is defined solely by the appended claims, and is not affected to any degree by the statements within this summary.

BRIEF DESCRIPTION OF THE DRAWINGS

FIG. 14 is a schematic view for describing a configuration according to a related art.

DETAILED DESCRIPTION OF THE PREFERRED EMBODIMENTS

First Embodiment

A sample measurement device 100 according to the present embodiment is a device that performs a first measurement and a second measurement in parallel. In recent years, various attempts have been made as a technique for examining a disease. As one of such techniques, a plurality of measurement results is combined. With this technique, a disease affecting the subject can be analyzed in more detail in some cases. For example, disseminated intravascular coagulation (DIC) can be appropriately diagnosed by combining a measurement result regarding a blood coagulation test and a measurement result regarding an immunological test. Specifically, the diagnosis of DIC is made on the basis of the coagulation time obtained from the measurement result regarding the blood coagulation test, and PIC, TAT, etc., obtained from the measurement result regarding the immunological test.

Hereinafter, the sample measurement device 100 that performs the first measurement related to the blood coagulation test and the second measurement related to the immunological test will be described.

<Configuration of Sample Measurement Device>

Figure 1:
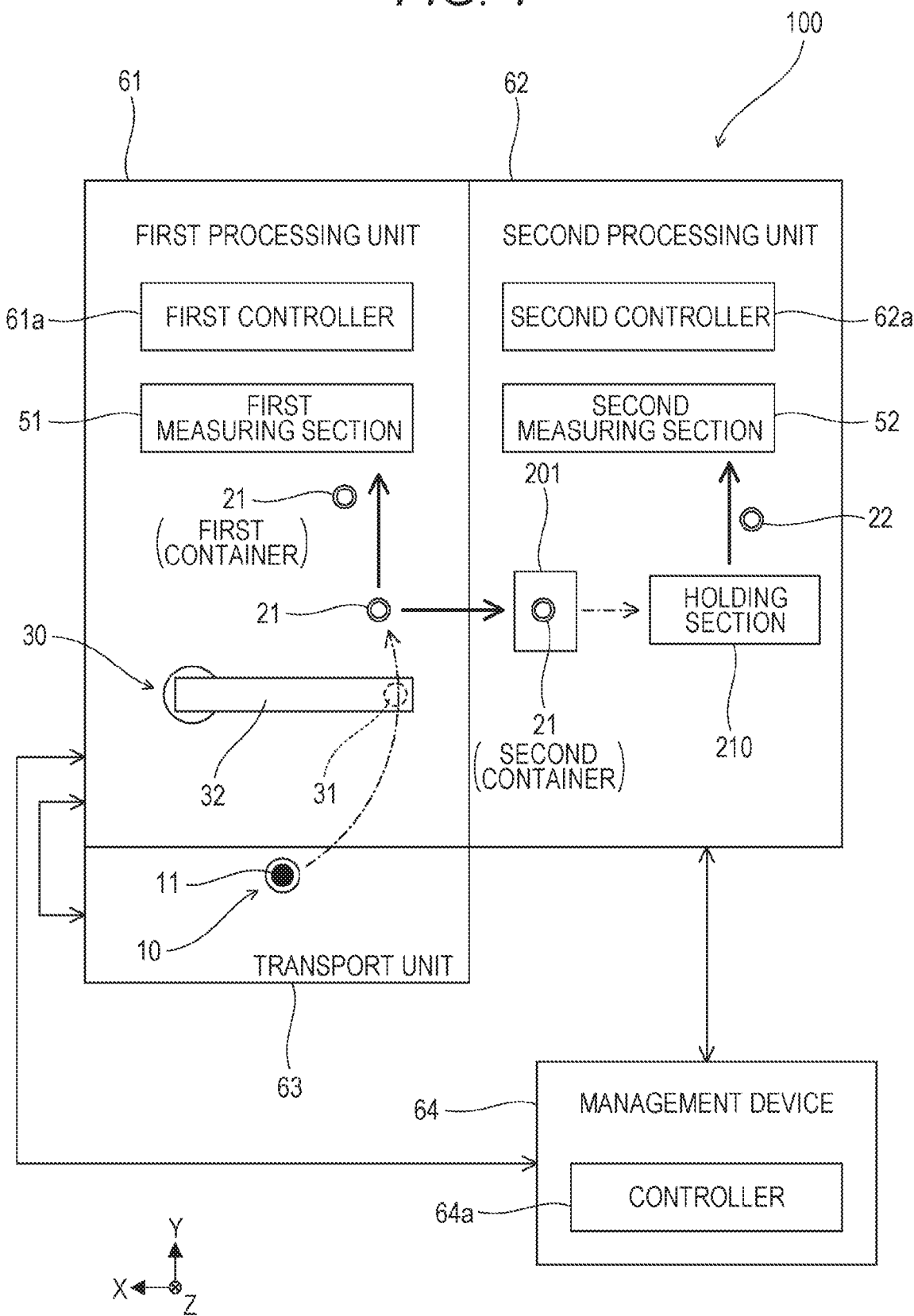
FIG. 1 is a diagram schematically showing a sample measurement device according to a first embodiment.

As shown in FIG. 1, the sample measurement device 100 includes a first processing unit 61, a second processing unit 62, a transport unit 63, and a management device 64. The first processing unit 61 is communicably connected to the transport unit 63 and the management device 64. The second processing unit 62 is communicably connected to the management device 64. In FIG. 1, XYZ axes are mutually orthogonal, the X-axis positive direction corresponds to the leftward direction, the Y-axis positive direction corresponds to the rearward direction, and the Z-axis positive direction corresponds to the vertically downward direction. In other figures, the XYZ axes are set similarly to FIG. 1.

The sample measurement device 100 measures a sample contained in a sample container 10.

As shown in FIG. 1, the first processing unit 61 includes a dispensing section 30, a first measuring section 51, and a first controller 61a. The first measuring section 51 performs a measurement related to a blood coagulation test as a first measurement. The dispensing section 30 includes a nozzle 31 and an arm 32. The nozzle 31 is a suction tube configured to be able to suck and discharge a sample. The nozzle 31 is provided at an end of the arm 32, and the arm 32 is configured to be pivotable. The dispensing section 30 dispenses the sample from the sample container 10 to a reaction container 21 using the nozzle 31. The first controller 61a controls each section of the first processing unit 61. The first controller 61a is composed of, for example, a CPU or a microcomputer.

The second processing unit 62 includes a second measuring section 52 and a second controller 62a. The second measuring section 52 performs a measurement related to an immunological test as a second measurement. The measurement related to the immunological test is a measurement related to a test different from the blood coagulation test. The measurement related to the immunological test includes a measurement of an immunological analysis item, a measurement by an immunological reaction, and the like. The measurement related to the immunological test indicates a measurement utilizing an antigen-antibody reaction. The second controller 62a controls each section of the second processing unit 62. The second controller 62a is composed of, for example, a CPU or a microcomputer.

The transport unit 63 includes a mechanism for transporting the sample container 10 to the first processing unit 61. The management device 64 is composed of, for example, a personal computer. The management device 64 includes a controller 64a. The controller 64a is composed of, for example, a CPU.

When the sample container 10 is located at a predetermined position, the dispensing section 30 sucks the sample in the sample container 10 through the tip of the nozzle 31. When the sample is sucked, the nozzle 31 is withdrawn from a stopper 11. Subsequently, the dispensing section 30 discharges the sample sucked from the sample container 10 to the reaction container 21.

When the measurement is performed on one sample by both the first measuring section 51 and the second measuring section 52, the dispensing section 30 dispenses the sample in the sample container 10 into two new reaction containers 21. Specifically, the dispensing section 30 repeats twice the dispensing operation of sucking the sample from the sample container 10 and discharging the sucked sample to a new reaction container 21. The sample first dispensed into the reaction container 21 is a sample that is to be measured by the first measuring section 51, and the sample dispensed next into the reaction container 21 is a sample that is to be measured by the second measuring section 52. The reaction container 21 into which the sample is first dispensed is a first container, and the reaction container 21 into which the sample is next dispensed is a second container. That is, the reaction containers 21 containing samples to be respectively measured by the first measuring section 51 and the second measuring section 52 are the first container 21 and the second container 21.

The first container 21 and the second container 21 may be the same or different in type.

The sample contained in the first container 21 is measured by the first measuring section 51 of the first processing unit 61, and the sample contained in the second container 21 is measured by the second measuring section 52 of the second processing unit 62.

The reaction container 21 is a so-called cuvette that is a container having an opening at the top. The reaction container 21, that is, the first container 21, is a disposable container used for a measurement in the first measuring section 51 of the first processing unit 61.

The first processing unit 61 transfers the reaction container 21, that is, the first container 21, into which the sample to be measured by the first measuring section 51 has been dispensed to the first measuring section 51. At this time, the first processing unit 61 prepares a measurement sample by adding a predetermined reagent to the first container, and transfers the first container 21 containing the measurement sample to the first measuring section 51. The first measuring section 51 irradiates the measurement sample in the first container 21 with light, and measures light transmitted through the measurement sample or light scattered by the measurement sample. Examples of the principle of the measurement by the first measuring section 51 include a coagulation method, a synthetic substrate method, an immunoturbidimetric method, and an agglutination method. The first controller 61a generates measurement data on the basis of the light measured by the first measuring section 51.

The first processing unit 61 transports the reaction container 21, that is, the second container 21, into which the sample to be measured by the second measuring section 52 has been dispensed to the second processing unit 62. At this time, the second container 21 is transferred from the first processing unit 61 to a relay section 201, then received by the second processing unit 62 from the relay section 201, and transferred to a predetermined position in the second measuring section 52.

When the reaction container 21, that is, the second container 21 in which the sample has been dispensed is transferred to the relay section 201 by the first processing unit 61, the second processing unit 62 receives the second container 21 from the relay section 201. Then, the second processing unit 62 transfers the second container 21 to a holding section 210 and holds the second container 21 therein.

The configuration of the relay section 201, the operation of the first processing unit 61 transferring the second container 21 to the relay section 201, and the operation of the second processing unit 62 receiving the reaction container 21 from the relay section 201 will be described later in detail.

The second processing unit 62 transfers the sample in the second container 21 transported from the first processing unit 61 to a reaction container 22. The reaction container 22 is a so-called cuvette that is a container having an opening at the top. The reaction container 22 is a disposable container used for the measurement in the second measuring section 52 of the second processing unit 62. The second processing unit 62 prepares a measurement sample by adding a predetermined reagent to the reaction container 22 into which the sample has been dispensed, and transfers the reaction container 22 containing the measurement sample to the second measuring section 52. The second measuring section 52 measures light generated from the measurement sample in the reaction container 22, that is, chemiluminescence based on a test substance contained in the sample. The second controller 62a generates measurement data on the basis of the light measured by the second measuring section 52.

Chemiluminescence is light emitted using the energy caused by a chemical reaction. For example, chemiluminescence is light emitted when a molecule is excited by a chemical reaction to be in an excited state and then returns to a ground state. In the embodiment, the chemiluminescence measured by the second measuring section 52 is light based on chemiluminescent enzyme immunoassay (CLEIA). Specifically, it is light generated by a reaction between an enzyme and a substrate. Chemiluminescence measured by the second measuring section 52 is, for example, light based on chemiluminescent immunoassay (CLIA), electrochemiluminescent immunoassay (ECLIA), fluorescent enzyme immunoassay (FEIA), luminescent oxygen channeling immunoassay (LOCI), bioluminescent enzyme immunoassay (BLEIA), or the like.

The controller 64a of the management device 64 performs an analysis on a blood coagulation test on the basis of the measurement data generated by the first processing unit 61. Specifically, the controller 64a performs an analysis on analysis items such as PT, APTT, Fbg, extrinsic coagulation factor, intrinsic coagulation factor, coagulation factor XIII, HpT, TTO, FDP, D dimer, PIC, FM, ATIII, Plg, APL, PC, VWF:Ag, VWF:RCo, ADP, collagen, or epinephrine.

The controller 64a performs an analysis related to an immunological test on the basis of the measurement data generated by the second processing unit 62. Specifically, the controller 64a performs an analysis on analysis items such as HBs antigen, HBs antibody, HBc antibody, HBe antigen, HBe antibody, HCV antibody, TP antibody, HTLV antibody, HIV antigen/antibody, TAT, PIC, TM, tPAI•c, TSH, FT3, or FT4.

When receiving the reaction container 21, that is, the second container 21, positioned at the relay section 201, the second controller 62a of the second processing unit 62 transmits a second signal indicating that the receiving operation is completed to the controller 64a. When receiving the second signal, the controller 64a transmits to the first controller 61a the first signal indicating that the second container 21 can be transferred to the relay section 201. These processes will be described later with reference to FIG. 9.

Subsequently, the configuration of the sample measurement device 100 will be described in detail separately for the first processing unit 61 and the second processing unit 62.

Figure 2:
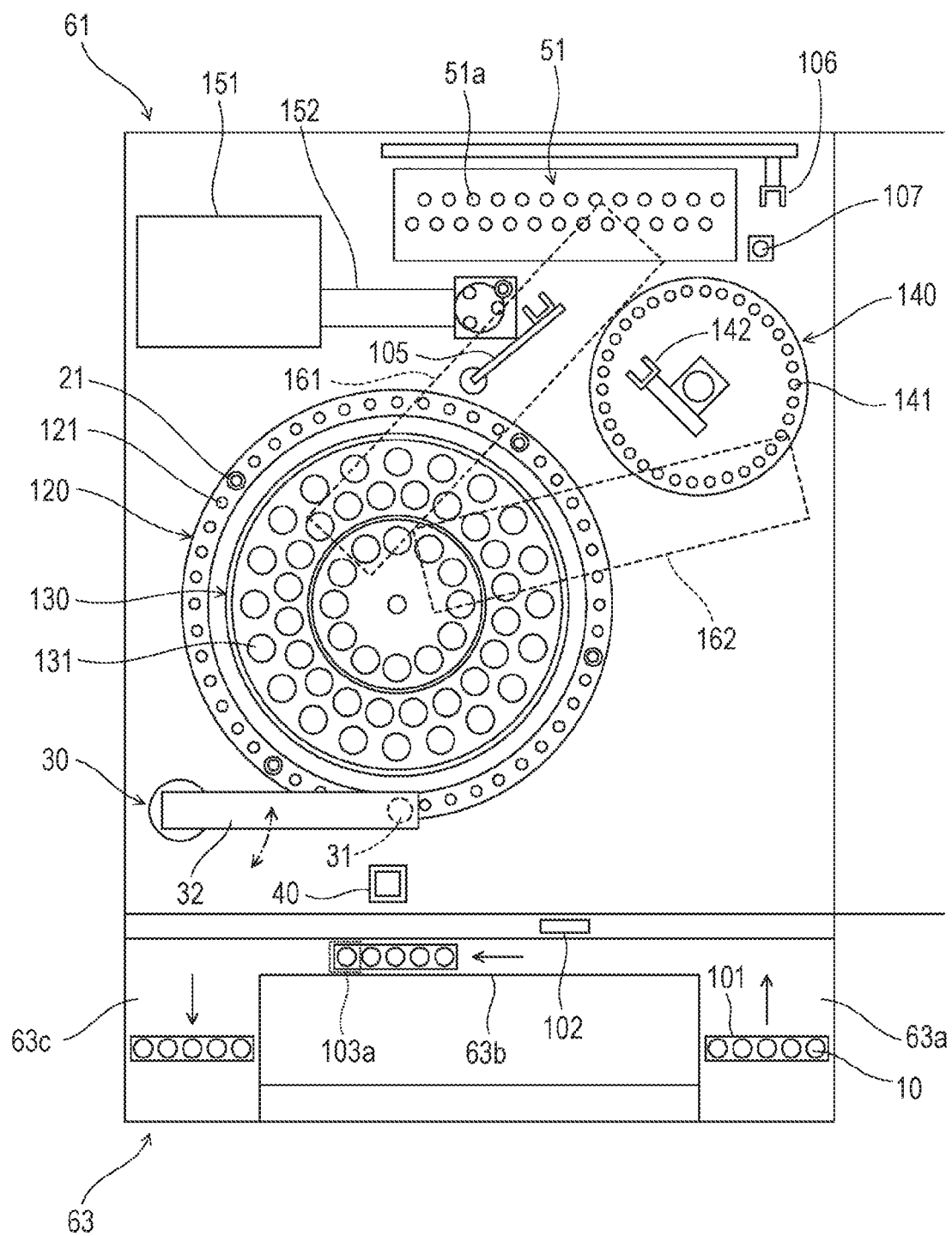
FIG. 2 is a view schematically showing a configuration of a first processing unit and a transport unit according to the first embodiment.

As shown in FIG. 2, the transport unit 63 has a rack setting position 63a, a rack transport area 63b, and a rack collecting position 63c. The rack setting position 63a and the rack collecting position 63c are connected to the right end and the left end of the rack transport area 63b, respectively. A barcode reader 102 is provided between the rack setting position 63a and the rack collecting position 63c. An operator places a sample rack 101 on which the sample container 10 is set at the rack setting position 63a.

The sample container 10 is, for example, a blood collection tube made of translucent glass or synthetic resin. A barcode label (not shown) is attached to the sample container 10. A barcode indicating a sample ID is printed on the barcode label. The sample ID is information that can individually identify the sample.

The transport unit 63 feeds the sample rack 101 installed at the rack setting position 63a to the right end of the rack transport area 63b, and further feeds the sample rack 101 to the front of the barcode reader 102. The barcode reader 102 reads the barcode from the barcode label on the sample container 10 and acquires the sample ID. The acquired sample ID is transmitted to the management device 64 for acquiring a measurement order for the sample.

Subsequently, the transport unit 63 transports the sample rack 101 holding the sample container 10, and sequentially positions the sample container 10 at a sample suction position 103a. The sample suction position 103a is a position at which the dispensing section 30 sucks a sample. When the suction of the samples contained in all sample containers 10 held in the sample rack 101 is finished, the transport unit 63 transports the sample rack 101 to the rack collecting position 63c.

The first processing unit 61 includes the dispensing section 30, a cleaning section 40, a reaction container table 120, a reagent table 130, a heating table 140, a transfer section 106, a reagent dispensing sections 161 and 162, the first measuring section 51, and a disposal port 107.

For the sample positioned at the sample suction position 103a, both the measurement order for performing the measurement related to the blood coagulation test in the first processing unit 61 and the measurement order for performing the measurement related to the immunological test in the second processing unit 62 are set.

The dispensing section 30 sucks the sample from the sample container 10 positioned at the sample suction position 103a. The dispensing section 30 sucks the sample from the sample container 10 twice and discharges the sucked sample to different reaction containers 21 in the reaction container table 120, respectively. At this time, the dispensing section 30 discharges the first sucked sample to the first container 21 as a sample to be subjected to a measurement related to a blood coagulation test, and discharges the next sucked sample to the second container 21 as a sample to be subjected to a measurement related to an immunological test. The operation of sucking the sample from the sample container 10 by the dispensing section 30 and the operation of discharging the sample sucked from the sample container 10 to the first container 21 and the second container 21 are performed as described with reference to FIG. 1.

The reaction container table 120 has a ring shape in a plan view, and is arranged outside the reagent table 130. The reaction container table 120 is configured to be rotatable in the circumferential direction. The reaction container table 120 has a plurality of holding holes 121 for holding the reaction container 21.

A reaction container storage section 151 stores a new reaction container 21. A reaction container supply section 152 takes out the reaction containers 21 one by one from the reaction container storage section 151, and supplies the reaction container 21 taken out from the reaction container storage section 151 to a holding position by the transfer section 105. The transfer section 105 holds the reaction container 21 supplied to the holding position by the reaction container supply section 152, and sets the reaction container 21 in the holding hole 121 of the reaction container table 120. The reaction container storage section 151 has a plurality of storage sections (not shown), and the reaction containers 21 are stored in the respective storage sections.

The cleaning section 40 is a vessel for cleaning the nozzle 31. When the dispensation for one sample container 10 is finished, the nozzle 31 is cleaned in the cleaning section 40.

The heating table 140 includes a plurality of holding holes 141 for holding the reaction container 21 and a transfer section 142 for transferring the reaction container 21. The heating table 140 has a circular shape in a plan view, and is configured to be rotatable in a circumferential direction. The heating table 140 heats the reaction container 21 set in the holding hole 141 to 37° C.

When the sample from the sample container 10 is discharged to the new reaction container 21 held in the reaction container table 120, the reaction container table 120 is rotated, and the reaction container 21, that is, the first container 21, is transferred to the vicinity of the heating table 140. Then, the transfer section 142 of the heating table 140 holds and sets the transferred first container 21 in the holding hole 141 of the heating table 140.

On the other hand, when the sample to be subjected to the second measurement is discharged to the new reaction container 21 held in the reaction container table 120, the reaction container table 120 is rotated, and the reaction container 21 is transferred to the vicinity of the heating table 140. This reaction container 21 is the second container 21. Then, the transfer section 142 of the heating table 140 holds and transports the second container 21 to the relay section 201 described later with reference to FIG. 3. That is, the second container 21 is transferred to the relay section 201 provided in the second processing unit 62 from the inside of the first processing unit 61 by the transfer section 142.

In the first processing unit 61, the reagent table 130 is configured so that a plurality of reagent containers 131 containing reagents used for measurement related to a blood coagulation test can be installed. The reagent table 130 is configured to be rotatable in the circumferential direction. The reagent dispensing sections 161 and 162 dispense the reagent into the reaction container 21 heated by the heating table 140.

The type of the reagent contained in the reagent container 131 differs depending on the measurement item. For example, when the time for blood to coagulate is measured, the prothrombin time (PT) of plasma is measured. In that case, Revohem (registered trademark) PT manufactured by Sysmex Corporation is used as the reagent.

When Revohem (registered trademark) PT is dispensed into the reaction container 21, the transfer section 142 of the heating table 140 takes out the reaction container 21 from the holding hole 141 of the heating table 140 and places this reaction container 21 at a predetermined position. Then, the reagent dispensing section 161 or the reagent dispensing section 162 sucks Revohem (registered trademark) PT from the reagent container 131 and discharges the sucked Revohem (registered trademark) PT to the reaction container 21. Thus, Revohem (registered trademark) PT is mixed with the sample. After that, the transfer section 106 sets the reaction container 21 in the holding hole 51a of the first measuring section 51.

The prothrombin time (PT) of the plasma described above is measured using a one-reagent system. In contrast, the D-D dimer in plasma or serum is measured using a two-reagent system. Specifically, in the measurement of D-D dimer, Lias Auto (registered trademark) D-dimer neo manufactured by Sysmex Corporation is used as a reagent.

In the measurement of the D-D dimer, first, the transfer section 142 of the heating table 140 takes out the reaction container 21, that is, the first container 21, from the holding hole 141 of the heating table 140, and positions this reaction container 21 at a predetermined position. Then, the reagent dispensing section 161 or the reagent dispensing section 162 sucks a D-dimer buffer (DDR1) from the reagent container 131 as a first reagent, and discharges the sucked D-dimer buffer (DDR1) to the reaction container 21. In this way, the D-dimer buffer (DDR1) is mixed with the sample. Thereafter, the transfer section 142 sets the reaction container 21 again in the holding hole 141 of the heating table 140.

Next, a D-dimer latex liquid (DDR2) is dispensed into the first container 21 as a second reagent. At this time, the transfer section 106 takes out the first container 21 from the holding hole 141 of the heating table 140 and positions this first container 21 at a predetermined position. Then, the reagent dispensing section 161 or the reagent dispensing section 162 sucks a D-dimer latex liquid (DDR2) from the reagent container 131, and discharges the sucked D-dimer latex liquid (DDR2) to the first container 21. In this way, the D-dimer latex liquid (DDR2) is mixed with the sample, and a measurement sample is prepared. Then, the transfer section 106 sets the first container 21 in the holding hole 51a of the first measuring section 51.

As described above, the measurement sample prepared by adding the reagent is set in the plurality of holding holes 51a of the first measuring section 51. The first measuring section 51 irradiates the first container 21 set in the holding hole 51a with light, and measures light transmitted through the measurement sample or light scattered by the measurement sample. When the measurement of the measurement sample in the reaction container 21 is completed, the first container 21 is discarded into the disposal port 107 by the transfer section 106.

Figure 3:
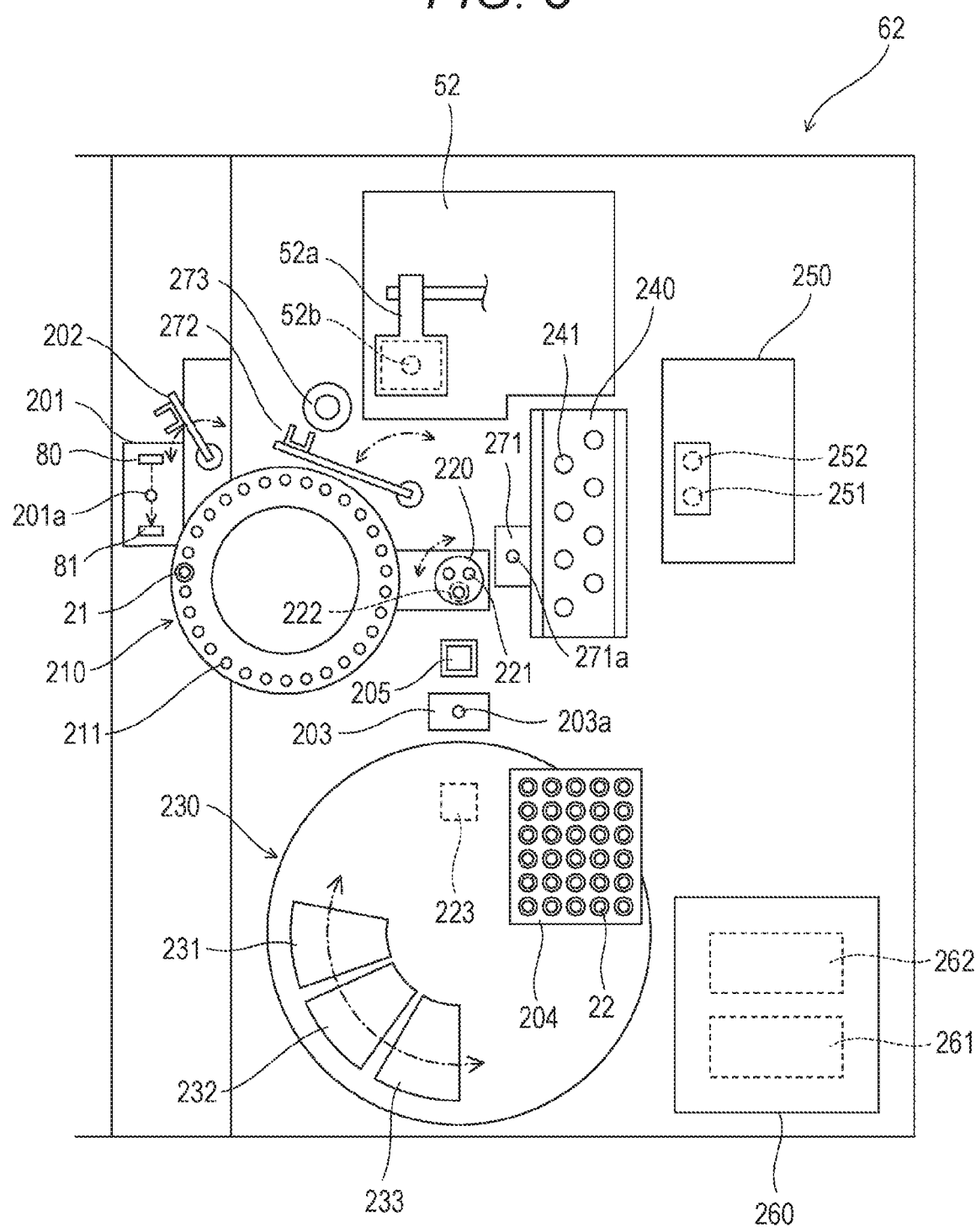
FIG. 3 is a view schematically showing a configuration of a second processing unit according to the first embodiment.

As shown in FIG. 3, the second processing unit 62 includes the relay section 201, a transfer section 202, a holding section 210, a delivery section 220, a storage section 203, a reaction container rack 204, a reagent table 230, a cleaning tank 205, a heating section 240, a reagent dispensing section 250, a reagent storage section 260, a storage section 271, a transfer section 272, a disposal port 273, and a second measuring section 52.

The relay section 201 is provided within the second processing unit 62. The relay section 201 includes a holding hole 201a for receiving the reaction container 21, that is, the second container 21. The reaction container 21, that is, the second container 21, is taken out from the holding hole 121 of the reaction container table 120, transported to the relay section 201, and set in the holding hole 201a by the transfer section 142 of the first processing unit 61.

The relay section 201 includes a light emitter 80 and a light receiver 81. The light emitter 80 and the light receiver 81 constitute a detector 201b which will be described later with reference to FIG. 7. The light emitter 80 and the light receiver 81 are arranged to face each other with the holding hole 201a interposed therebetween. Light emitted from the light emitter 80 is received by the light receiver 81.

When the second container 21 is positioned in the holding hole 201a of the relay section 201, light emitted from the light emitter 80 is blocked by the second container 21 and is not received by the light receiver 81. On the other hand, when the second container 21 is not positioned in the holding hole 201a, light from the light emitter 80 is received by the light receiver 81. In this way, the presence or absence of the second container 21 in the relay section 201 can be determined on the basis of whether or not the light receiver 81 receives light emitted from the light emitter 80.

The holding section 210 includes a plurality of holding holes 211. The holding section 210 has a circular shape in a plan view, and is configured to be rotatable in the circumferential direction. The second container 21 positioned in the relay section 201 is transferred to the holding section 210 and is set in the holding hole 211 by the transfer section 202. In this way, the second container 21 is set in the holding section 210 from the first processing unit 61 via the relay section 201.

Figure 4:
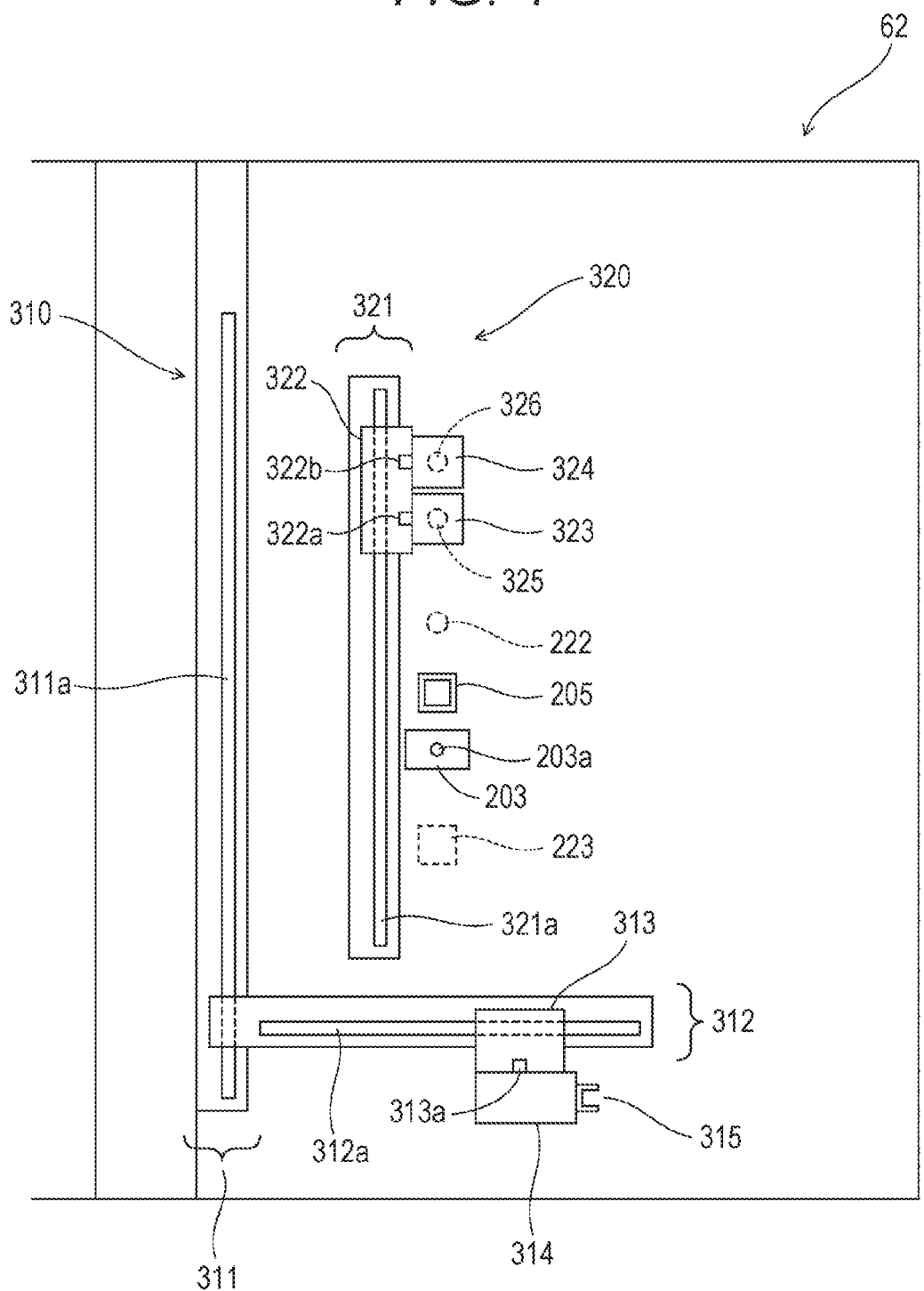
FIG. 4 is a view schematically showing a configuration of a transfer section and a dispensing section according to the first embodiment.

The second processing unit 62 further includes a transfer section 310 and a dispensing section 320 illustrated in FIG. 4 in addition to the sections illustrated in FIG. 3. The transfer section 310 is installed on a wall surface inside the first processing unit 61 parallel to the YZ plane, and the dispensing section 320 is installed on the ceiling surface of the second processing unit 62.

As shown in FIG. 4, the transfer section 310 includes a front-rear transfer part 311, a horizontal transfer part 312, a vertical transfer part 313, a support member 314, and a holding part 315. The front-rear transfer part 311 transfers the horizontal transfer part 312 in the Y-axis direction along a rail 311a extending in the Y-axis direction by driving a stepping motor. The horizontal transfer part 312 transfers the vertical transfer part 313 in the X-axis direction along a rail 312a extending in the X-axis direction by driving a stepping motor. The vertical transfer part 313 transfers the support member 314 in the Z-axis direction along a rail 313a extending in the Z-axis direction by driving a stepping motor. The holding part 315 is provided on the support member 314. The holding part 315 is configured to be able to hold the second container 21 and the reaction container 22.

The transfer section 310 transfers the holding part 315 in the X-, Y-, and Z-axis directions in the first processing unit 61 by driving the front-rear transfer part 311, the horizontal transfer part 312, and the vertical transfer part 313. Thus, the second container 21 and the reaction container 22 can be transferred in the second processing unit 62.

The dispensing section 320 includes a front-rear transfer part 321, a vertical transfer part 322, support members 323 and 324, and nozzles 325 and 326. The front-rear transfer part 321 transfers the vertical transfer part 322 in the Y-axis direction along a rail 321a extending in the Y-axis direction by driving a stepping motor. The vertical transfer part 322 moves the support member 323 in the Z-axis direction along a rail 322a extending in the Z-axis direction, and to move the support member 324 in the Z-axis direction along a rail 322b extending in the Z-axis direction, by driving a stepping motor.

The nozzles 325 and 326 are installed on support members 323 and 324, respectively, so as to be adjacent to each other in the Y-axis direction. The nozzles 325 and 326 extend in the Z-axis direction, and the tips of the nozzles 325 and 326 are directed in the Z-axis positive direction. The nozzle 325 is used for dispensing a sample, and the nozzle 326 is used for dispensing a reagent.

When the reaction container 21 is set in the holding hole 211 of the holding section 210, the reaction container 21 is taken out from the holding hole 211 and set in the holding hole 221 of the delivery section 220 by the transfer section 310. The delivery section 220 includes three holding holes 221. The delivery section 220 has a circular shape in a plan view, and is configured to be rotatable in a circumferential direction. When the second container 21 is set in the holding hole 221 of the delivery section 220, the delivery section 220 is rotated in the circumferential direction, and the second container 21 is positioned at a sample suction position 222.

The reaction container rack 204 stores 30 new reaction containers 22. The storage section 203 includes a holding hole 203a for holding the reaction container 22.

The transfer section 310 takes out the reaction container 22 from the reaction container rack 204 and sets it in the holding hole 203a. Then, the dispensing section 320 sucks the sample in the reaction container 21 positioned at the sample suction position 222 using the nozzle 325, and discharges the sucked sample to the reaction container 22 set in the holding hole 203a. Thus, the sample is transferred from the second container 21 to the reaction container 22. After the sample is transferred, the nozzle 325 is cleaned in the cleaning tank 205. The second container 21 from which the sample has been completely transferred is discarded into the disposal port 273 by the transfer section 272.

Next, the measurement related to an immunological test will be described in detail with reference to FIGS. 3 and 4.

As shown in FIG. 3, the reagent table 230 is configured such that reagent containers 231 to 233 containing reagents used for the measurement related to the immunological test can be installed. The reagent table 230 is configured to be rotatable in the circumferential direction. The reagent container 231 contains an R1 reagent, the reagent container 232 contains an R2 reagent, and the reagent container 233 contains an R3 reagent.

As shown in FIG. 4, the transfer section 310 takes out the reaction container 22 containing the sample from the holding hole 203a and positions this reaction container 22 above the cleaning tank 205. In this state, the dispensing section 320 sucks the R1 reagent from the reagent container 231 positioned at a reagent suction position 223 using the nozzle 326, and discharges the sucked R1 reagent into the reaction container 22 positioned above the cleaning tank 205. After the R1 reagent is dispensed, the nozzle 326 is cleaned in the cleaning tank 205.

As shown in FIG. 3, the heating section 240 includes a plurality of holding holes 241 for heating the reaction container 22. The transfer section 310 sets the reaction container 22 into which the R1 reagent has been discharged into the holding hole 241 of the heating section 240. After the reaction container 22 is heated by the heating section 240 for a predetermined time, the transfer section 310 takes out the reaction container 22 from the holding hole 241 and positions this reaction container 22 above the cleaning tank 205. In this state, the dispensing section 320 sucks the R2 reagent from the reagent container 232 positioned at the reagent suction position 223 using the nozzle 326, and discharges the sucked R2 reagent into the reaction container 22 positioned above the cleaning tank 205. After the R2 reagent is dispensed, the nozzle 326 is cleaned in the cleaning tank 205.

As shown in FIG. 4, the transfer section 310 places the reaction container 22 into which the R2 reagent has been discharged into the holding hole 241 of the heating section 240. The heating section 240 heats the reaction container 22 for a predetermined time.

The R1 reagent contains a capturing substance that binds to the test substance, and the R2 reagent contains magnetic particles. When the R1 reagent and the R2 reagent are discharged into the reaction container 22, and this reaction container 22 is heated in the heating section 240, the test substance, which is contained in the second container, within the reaction container 22 binds to the magnetic particles via the capturing substance by the antigen-antibody reaction. Thus, a complex in which the test substance and the magnetic particles are bound is generated.

The transfer section 310 positions the reaction container 22 into which the R2 reagent has been discharged and which has been heated to a location above the cleaning tank 205. In this state, the dispensing section 320 sucks the R3 reagent from the reagent container 233 positioned at the reagent suction position 223 using the nozzle 326, and discharges the sucked R3 reagent into the reaction container 22 positioned above the cleaning tank 205. Then, the transfer section 310 sets the reaction container 22 into which the R3 reagent has been discharged into the holding hole 241 of the heating section 240. The heating section 240 heats the reaction container 22 for a predetermined time.

The R3 reagent includes a labeled antibody which uses an antibody as a capturing substance. When the R3 reagent is discharged into the reaction container 22 and this reaction container 22 is heated by the heating section 240, a complex in which the test substance, the capturing antibody, the magnetic particles, and the labeled antibody are bound is generated.

The transfer section 310 positions the reaction container 22 directly below a nozzle 251 of the reagent dispensing section 250. The reagent dispensing section 250 includes the nozzle 251 for discharging an R4 reagent, and a nozzle 252 for discharging an R5 reagent. The reagent dispensing section 250 also includes a mechanism for moving the nozzles 251 and 252 in the Z-axis direction.

As shown in FIG. 3, the reagent dispensing section 250 discharges the R4 reagent into the reaction container 22 through the nozzle 251. Subsequently, the transfer section 310 positions the reaction container 22 into which the R4 reagent has been discharged directly below the nozzle 252. The reagent dispensing section 250 discharges the R5 reagent into the reaction container 22 through the nozzle 252. The R4 reagent and the R5 reagent are contained in reagent containers 261 and 262, respectively, which are installed in the reagent storage section 260, and the nozzles 251 and 252 are connected to the reagent containers 261 and 262, respectively, by a flow path (not shown).

The R4 reagent is a reagent for dispersing the complex in the reaction container 22. When the complex and the R4 reagent are mixed, the complex is dispersed in the reaction container 22. The R5 reagent is a reagent containing a luminescent substrate that generates light by reaction with the labeled antibody bound to the complex. When the complex and the R5 reagent are mixed, chemiluminescence is generated by the reaction between the labeled antibody bound to the complex and the luminescent substrate. Thus, the preparation of the measurement sample used for the first measurement is completed.

As shown in FIG. 4, the transfer section 310 places the reaction container 22 into which the R5 reagent has been discharged into the holding hole 241 of the heating section 240. After the reaction container 22 is heated by the heating section 240 for a predetermined time, the transfer section 310 takes out the reaction container 22 from the holding hole 241 and sets it into a holding hole 271a formed in the storage section 271.

The second measuring section 52 includes a lid 52a and a holding hole 52b. The lid 52a is configured to be openable and closable above the holding hole 52b. When the reaction container 22 is set in the holding hole 271a, the lid 52a is opened, and the transfer section 272 takes out the reaction container 22 from the holding hole 271a and sets it in the holding hole 52b of the second measuring section 52. Then, the lid 52a is closed, and light generated from the measurement sample in the reaction container 22 is measured in the holding hole 52b. When the measurement of the measurement sample in the reaction container 22 is completed, the reaction container 22 is discarded into the disposal port 273 by the transfer section 272.

Figure 5A:
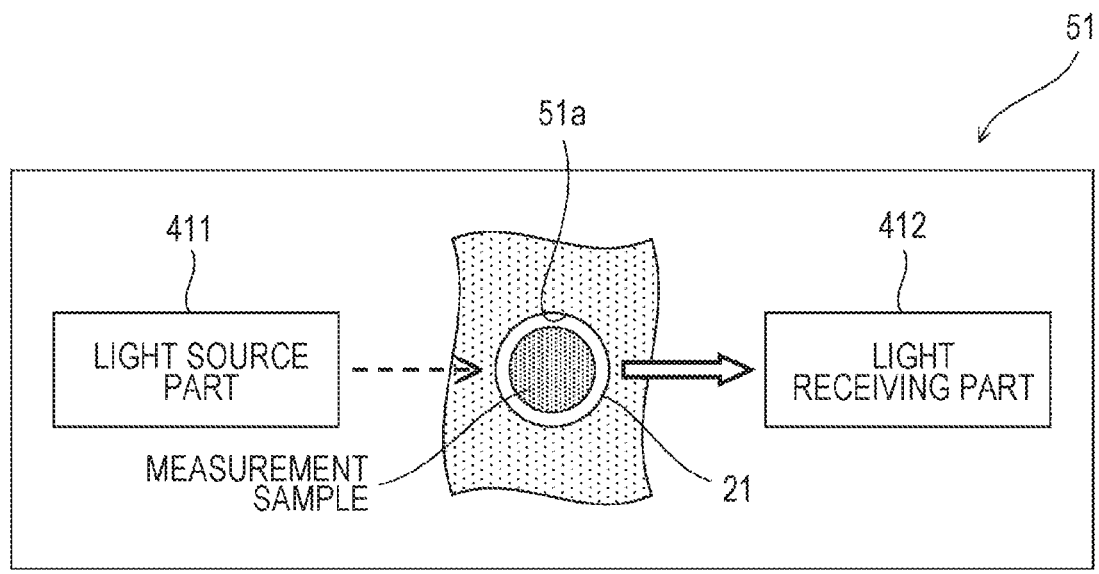
FIGS. 5A and 5B are views schematically showing a configuration of a first measuring section and a second measuring section according to the first embodiment.

As shown in FIG. 5A, the first measuring section 51 that performs a measurement related to a blood coagulation test includes a light source part 411 and a light receiving part 412 in addition to the above-described holding holes 51a. FIG. 5A shows the periphery of one holding hole 51a among the plurality of holding holes 51a.

The light source part 411 includes a semiconductor laser light source. The light source part 411 emits light beams of different wavelengths. The light source part 411 irradiates the first container 21 set in each holding hole 51a with light. When the measurement sample in the first container 21 is irradiated with light, light transmitted through the measurement sample or light scattered by the measurement sample enters the light receiving part 412. The light receiving part 412 which is composed of a photodetector is provided for each holding hole 51a. Specifically, the light receiving part 412 includes a phototube, a photodiode, and the like. The light receiving part 412 receives transmitted light or scattered light and outputs an electric signal corresponding to the amount of received light. The first controller 61a generates measurement data used for an analysis related to a blood coagulation test on the basis of the electric signal output from the light receiving part 412.

Figure 5B:
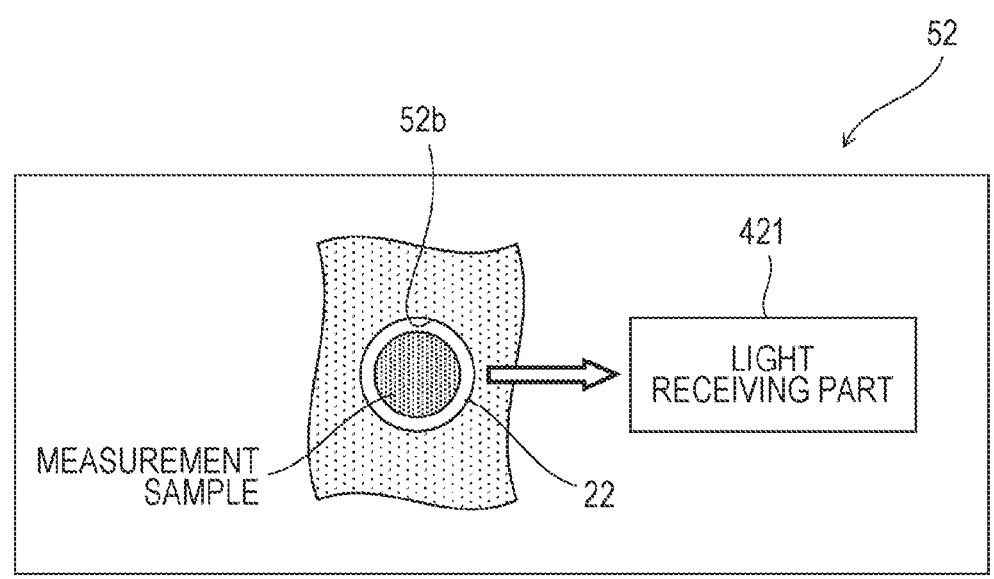

As shown in FIG. 5B, the second measuring section 52 that performs a measurement related to the immunological test includes a light receiving part 421 in addition to the above-described holding hole 52b. FIG. 5B shows the periphery of the holding hole 52b.

Chemiluminescence generated from the measurement sample contained in the reaction container 22 enters the light receiving part 421. The light receiving part 421 is composed of a photodetector capable of counting photons. Specifically, the light receiving part 421 includes a photomultiplier tube. When the light receiving part 421 includes a photomultiplier tube capable of counting photons, the second measuring section 52 can perform highly sensitive and highly accurate measurement. The light receiving part 421 receives the chemiluminescence and outputs a pulse waveform corresponding to the received photons. The second measuring section 52 counts photons at regular intervals on the basis of the output signal of the light receiving part 421 and outputs a count value by a circuit provided therein. The second controller 62a generates measurement data used for an analysis related to an immunological test on the basis of the count value output from the second measuring section 52.

Figure 6:
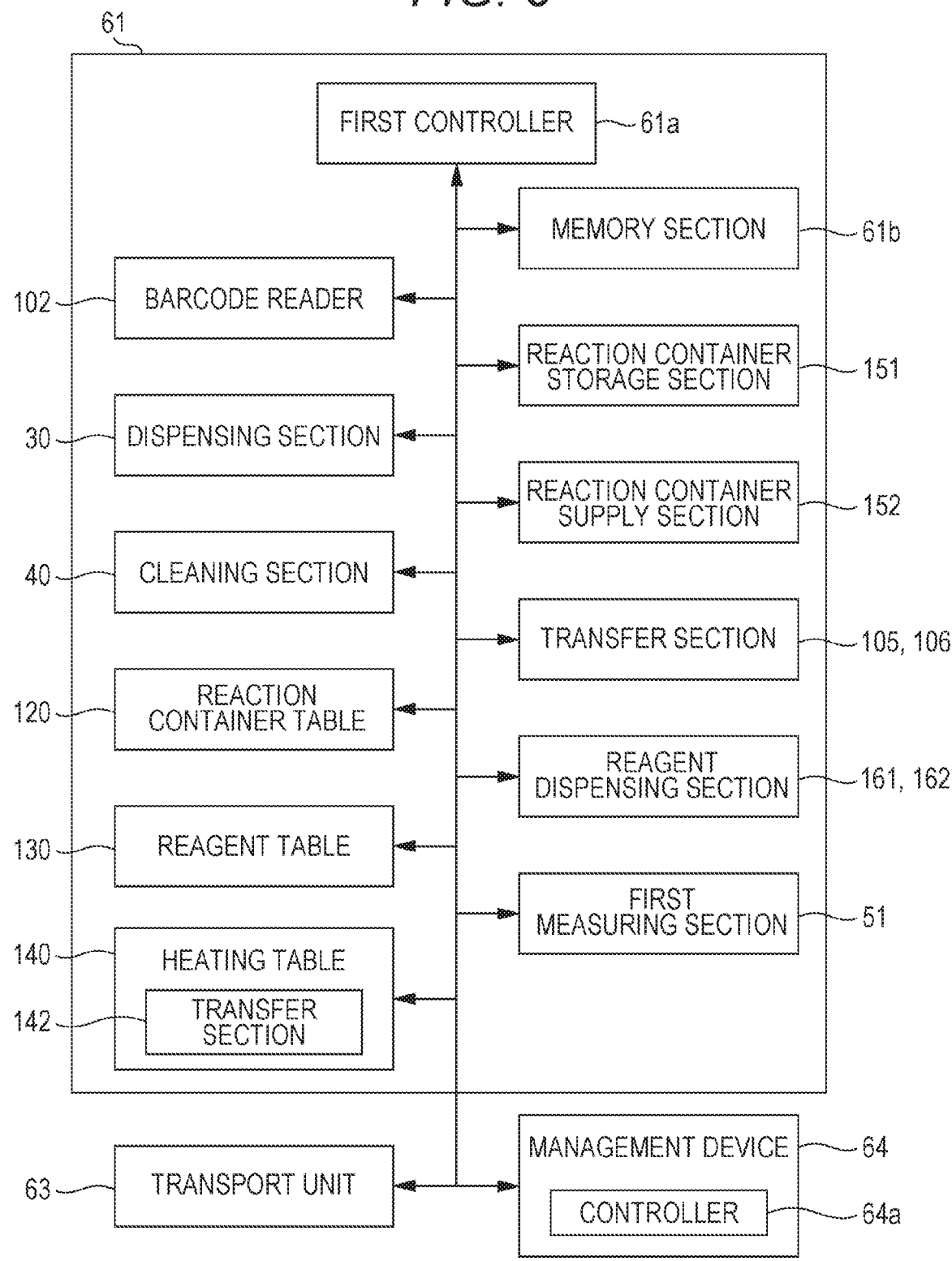
FIG. 6 is a diagram schematically showing a circuit configuration of the first processing unit according to the first embodiment.

As shown in FIG. 6, the first processing unit 61 includes, as the configuration of a circuit section, the first controller 61a, a memory section 61b, the barcode reader 102, the dispensing section 30, the cleaning section 40, the reaction container table 120, the reagent table 130, the heating table 140, the reaction container storage section 151, the reaction container supply section 152, the transfer sections 105 and 106, the reagent dispensing sections 161 and 162, and the first measuring section 51.

The first controller 61a controls each section in the first processing unit 61 and the transport unit 63 according to a program stored in the memory section 61b. The memory section 61b includes a ROM, a RAM, a hard disk, and the like. The first controller 61a is configured to be able to communicate with the transport unit 63 and the controller 64a of the management device 64.

Figure 7:
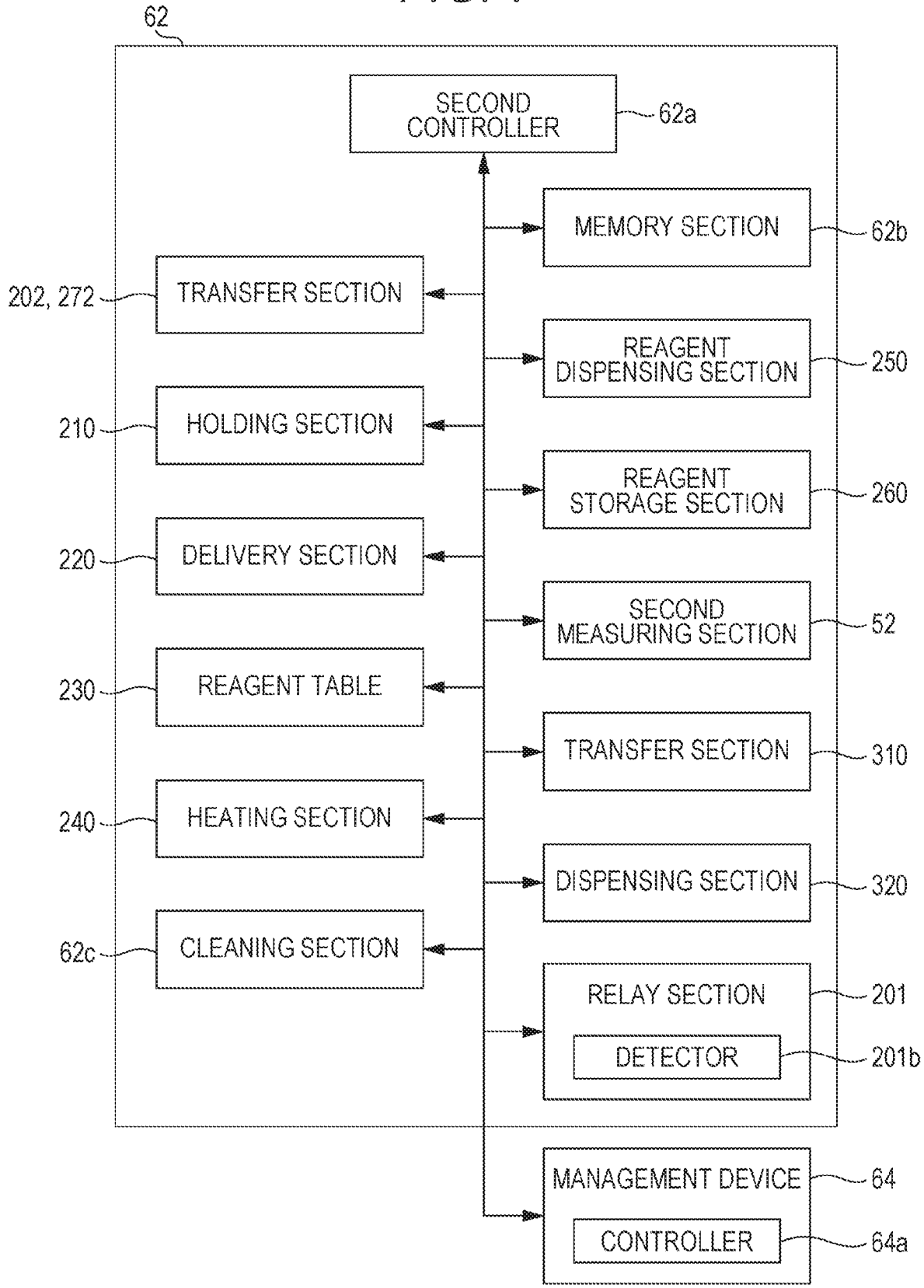
FIG. 7 is a diagram schematically showing a circuit configuration of the second processing unit according to the first embodiment.

As shown in FIG. 7, the second processing unit 62 includes, as a configuration of a circuit section, the second controller 62a, a memory section 62b, the cleaning section 62c, the relay section 201, the transfer sections 202 and 272, the holding section 210, the delivery section 220, the reagent table 230, the heating section 240, the reagent dispensing section 250, the reagent storage section 260, the second measuring section 52, the transfer section 310, and the dispensing section 320.

The second controller 62a controls each section in the second processing unit 62 according to a program stored in the memory section 62b. The memory section 62b includes a ROM, a RAM, a hard disk, and the like. The cleaning tank 205 described with reference to FIG. 3, the flow path and the mechanism for flowing the cleaning liquid through the cleaning tank 205 and the nozzles 325 and 326 are included in the cleaning section 62c.

The relay section 201 includes the detector 201b. The detector 201b detects that the reaction container 21 is positioned in the relay section 201. As described with reference to FIG. 3, the detector 201b includes the light emitter 80 and the light receiver 81.

The processing of the sample measurement device 100 will be described with reference to the flowchart shown in FIG. 8. The following description starts from the activation of the sample measurement device 100. The second container 21 is not positioned in the relay section 201, and the holding hole 201a is vacant.

Figure 8:
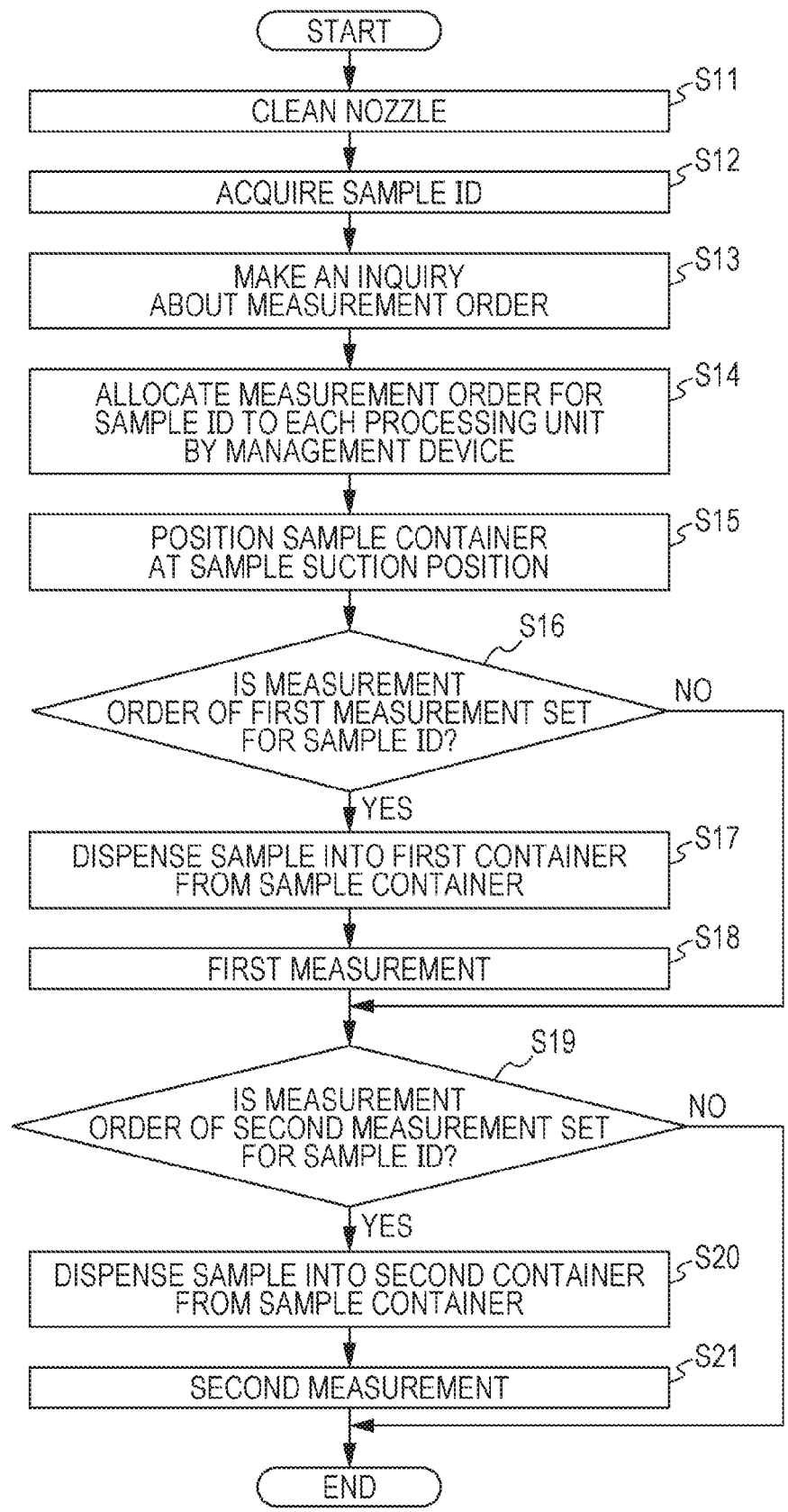
FIG. 8 is a flowchart showing a process of the sample measurement device according to the first embodiment.

As shown in FIG. 8, when the sample measurement device 100 is started, the first controller 61a drives the dispensing section 30 and the cleaning section 40 to clean the nozzle 31 of the dispensing section 30 in step S11. In step S12, the first controller 61a drives the transport unit 63 to transport the sample container 10 to the front of the barcode reader 102, and drives the barcode reader 102 to acquire the sample ID from the barcode label of the sample container 10. In step S13, the first controller 61a makes an inquiry about the measurement order to the controller 64a on the basis of the sample ID acquired in step S12.

In step S14, the controller 64a allocates the measurement order corresponding to the sample ID inquired by the first controller 61a to the first controller 61a and the second controller 62a. For example, if the measurement order of the second measurement, that is, the measurement related to immunity, is set for the sample of the sample ID inquired by the first controller 61a, the controller 64a allocates combined information of the sample ID and the measurement order of the second measurement to the second controller 62a. The allocated information is stored in the memory section 62b.

On the other hand, the controller 64a allocates combined information of the sample ID inquired by the first controller 61a and the measurement order to the first controller 61a. The measurement order allocated to the first controller 61a includes the measurement order of the second measurement. The allocated information is stored in the memory section 61b.

Subsequently, in step S15, the first controller 61a drives the transport unit 63 to position the sample container 10 at the sample suction position 103a.

In step S16, the controller 64a determines whether a measurement order related to the blood coagulation test as the first measurement has been set for the sample ID associated with the sample container 10 at the sample suction position 103a.

In step S17, when the measurement order related to the blood coagulation test is set for the sample ID associated with the sample container 10, the controller 64a causes the first controller 61a to drive the dispensing section 30 to suck the sample in the sample container 10 and to discharge the sucked sample into a new reaction container 21, that is, the first container 21, held in the reaction container table 120.

The sample dispensed in step S17 is a sample used for the measurement of a blood coagulation test, and is a sample stored in the first container 21 as described above. In step S18, the controller 64a controls the first controller 61a such that the first measurement is performed on the first sample by the first measuring section 51. On the other hand, if the measurement order related to the blood coagulation test is not set, the processes in steps S17 and S18 are skipped.

In step S19, the controller 64a determines whether a measurement order related to an immunological test as the second measurement has been set for the sample ID associated with the sample container 10 at the sample suction position 103a.

When the measurement order related to the immunological test is set, the controller 64a causes the first controller 61a to drive the dispensing section 30 to suck the sample in the sample container 10 and to discharge the sucked sample into a new reaction container 21, that is, the second container 21, held in the reaction container table 120 in step S20. The sample dispensed in step S20 is a sample used for the measurement of the immunological test, and is a sample stored in the second container 21 as described above.

In step S21, the controller 64a controls the second controller 62a such that the second measurement is performed on the sample contained in the second container 21 by the second measuring section 52. On the other hand, if the measurement order related to the immunological test has not been set, the processes in steps S20 and S21 are skipped.

When the process is completed for one sample container 10 positioned at the sample suction position 103a, the process routine returns to step S11. Accordingly, in step S11, the first controller 61a cleans the nozzle 31 of the dispensing section 30. After that, the first controller 61a performs the processes in steps S12 to S21 on the subsequent sample container 10.

The second measurement in the above step S21 includes a process of transferring the second container 21 containing the sample to the relay section 201 from the first processing unit 61, and receiving the second container 21 from the relay section 201 by the second processing unit 62 as described with reference to FIGS. 1 to 3. The transfer of the second container 21 from the first processing unit 61 to the second processing unit 62 will be described below with reference to FIGS. 9A to 9C.

Figure 9A:
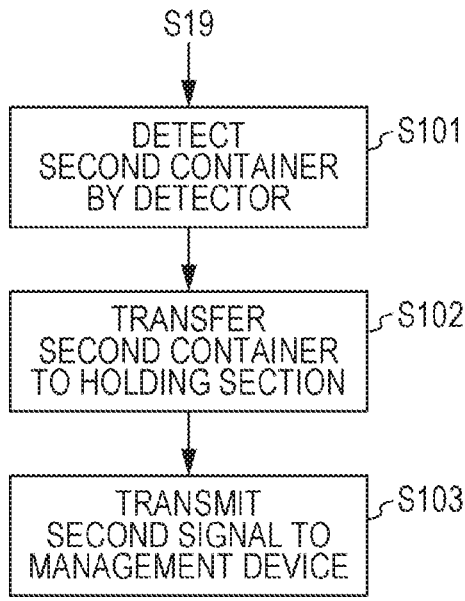
FIG. 9A is a flowchart showing a process when the second processing unit receives a second container from a relay section in the first embodiment.

As shown in FIG. 9A, in step 5101, the first controller 61a drives the transfer section 142 to transfer the second container 21 to the relay section 201. This second container stores the sample dispensed from the sample container 10 in step S19 in FIG. 8. When the second container 21 is transferred to the relay section 201, that is, when the second container 21 is positioned in the holding hole 201a of the relay section 201, light from the light emitter 80 is blocked by the second container 21. Therefore, the light from the light emitter 80 is not received by the light receiver 81. The light receiver 81 outputs to the second controller 62a a signal indicating that the light from the light emitter 80 is not received. This signal indicates that the second container 21 is positioned in the relay section 201. The light receiver 81 transmits this signal to the second controller 62a. Thus, the situation in which the second container 21 is positioned in the relay section 201 is transmitted to the second controller 62a.

When the signal indicating that the second container 21 is present in the relay section 201 is transmitted from the light receiver 81, that is, the detector 201b, to the second controller 62a in step S101, the second controller 62a drives the transfer section 202 at an arbitrary timing to execute the receiving operation of receiving the second container 21 from the relay section 201 in step S102. Then, the second controller 62a transfers the second container 21 to the holding section 210. That is, the second container 21 is set in the predetermined holding hole 211 of the holding section 210. Thus, the reception of the second container 21 by the second processing unit 62 is completed.

In step S103, the second controller 62a transmits the second signal indicating that the reception of the second container 21 from the relay section 201 has been completed to the controller 64a. In step S14 in FIG. 8, the combined information of the sample ID and the measurement order is allocated by the controller 64a and sorted in the memory section 62b. For this reason, the second processing unit 62 knows the sample ID and the measurement order of the sample contained in the second container 21 to be transported to the second processing unit 62. Therefore, when transmitting the second signal to the controller 64a, the second controller 62a also transmits the information about the sample ID of the sample contained in the received second container 21 and the measurement order. Accordingly, the controller 64a causes a memory section 64b to store information indicating that the second container 21 has been transported to the second processing unit 62.

In step S103 in FIG. 9A, the fact that the second signal is transmitted from the second controller 62a to the controller 64a means that the holding hole 201a of the relay section 201 is vacant. Therefore, it is possible to transfer the new second container 21 from the first processing unit 61 to the relay section 201.

Figure 9B:
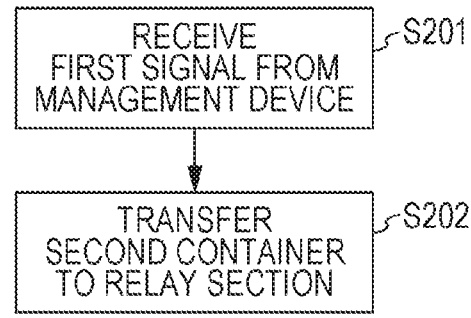
FIG. 9B is a flowchart showing a process when the first processing unit transfers the second container to the relay section in the first embodiment.

As shown in FIG. 9B, the controller 64a transmits to the first controller 61a the first signal indicating that the second container 21 can be transferred to the relay section 201 in step S201.

In step S202, when the first signal is transmitted from the controller 64a, the first controller 61a drives the transfer section 142 at an arbitrary timing to position the second container 21 in the relay section 201.

Figure 9C:
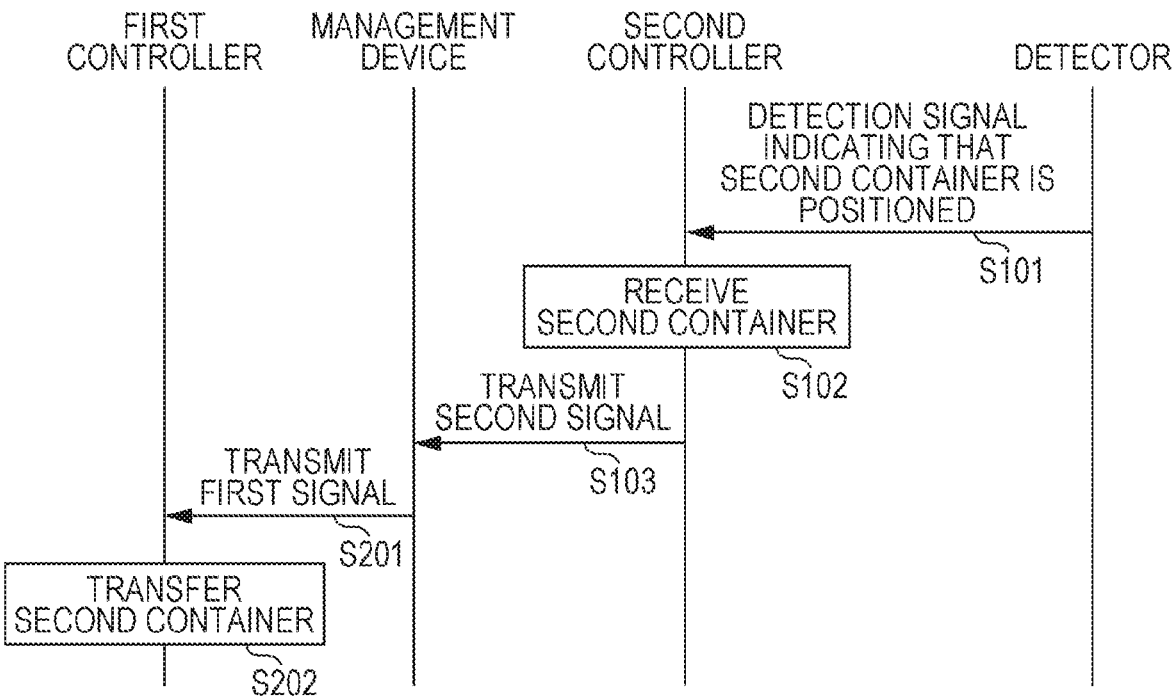
FIG. 9C is a sequence diagram indicating the processes shown in FIGS. 9A and 9B.

FIG. 9C is a sequence diagram showing the processes in the first processing unit 61 and the second processing unit 62 described with reference to FIGS. 9A and 9B. As shown in FIG. 9C, when detecting that the second container 21 is positioned in the relay section 201, the detector 201b transmits a signal indicating that the second container 21 is positioned in the relay section 201 to the second controller 62a (S101). On the basis of this signal, the second controller 62a performs a receiving operation of receiving the second container 21 from the relay section 201 by driving the transfer section 202, and transfers the second container 21 to the holding section 210 (S102). After performing the receiving operation, the second controller 62a transmits, to the controller 64a, the second signal indicating that the second container 21 has been received from the relay section 201 together with the information regarding the sample (S103).

When receiving the second signal, the controller 64a transmits to the first controller 61a the first signal indicating that the second container 21 can be transferred to the relay section 201 (S201). When receiving the first signal, the first controller 61a executes the transferring operation of transferring the second container 21 containing the sample to the relay section 201 by driving the transfer section 142 (S202).

As described above, the second container 21 is transferred from the first processing unit 61 to the second processing unit 62 via the relay section 201.

Effects of First Embodiment

As shown in FIGS. 1, 3, and 7, in the sample measurement device 100, the second container 21 to be subjected to the second measurement is transported from the first processing unit 61 to the second processing unit 62 via the relay section 201. Accordingly, the first processing unit 61 and the second processing unit 62 can transfer the second container 21 to the relay section 201 and receive the reaction container 21 from the relay section at a preferable timing for the respective processing units without being affected by each other's operating statuses.

Since the first processing unit 61 and the second processing unit 62 can access the relay section 201 at a preferable timing for each processing unit without being affected by each other's operating statuses, the second container 21 can be transferred from the first processing unit 61 to the second processing unit 62 even if first and second measurement cycles are different from each other.

The "measurement cycle" indicates a time required for measuring a sample. The measurement cycle is the total time required for each step included in one measurement. For example, if the first measurement includes a step of dispensing a reagent to the sample, a step of stirring the sample, a step of heating the sample, a step of centrifugation, and a step of performing a measurement for a predetermined measurement item, the first cycle in the first measurement indicates a time required to complete these five steps.

For example, in a case where the time required for the first measurement and the time required for the second measurement are 40 seconds and 320 seconds, respectively, and the relay section 201 is not provided in the sample measurement device 100, the first processing unit 61 can transfer the second container 21 to the second processing unit 62 every 40 seconds. However, the second processing unit 62 cannot receive the second container 21 until after 320 seconds. Therefore, in a case where the relay section 201 is not provided in the sample measurement device 100, the first processing unit 61 needs to be configured to transfer the second container 21 to the second processing unit 62 after waiting for 270 seconds. That is, it is necessary to synchronize the operations of the first processing unit 61 and the second processing unit 62.

In this case, if the operations of the first processing unit 61 and the second processing unit 62 are slightly shifted, the second container 21 cannot be transferred from the first processing unit 61 to the second processing unit 62. Therefore, control for synchronizing the operations of the first processing unit 61 and the second processing unit 62 needs to be set strictly, and such control is complicated.

On the other hand, the sample measurement device 100 according to the first embodiment includes the relay section 201, and thus, the first processing unit 61 and the second processing unit 62 can transfer and receive the reaction container 21 to and from the relay section 201 at an arbitrary timing. Therefore, there is no need to perform synchronous control of the first processing unit 61 and the second processing unit 62. Accordingly, the control of the sample measurement device 100 is not complicated.

The time required for one measurement in the first processing unit 61 and the time required for one measurement in the second processing unit 62 may be the same.

As shown in FIGS. 1 and 2, in the sample measurement device 100, the sample to be subjected to the second measurement is dispensed into the second container 21 by the dispensing section 30 disposed in the first processing unit 61. As described above, in the sample measurement device 100 provided with two processing units, the dispensing section 30 is shared, whereby an increase in size of the sample measurement device 100 can be prevented.

As shown in FIG. 3, the second processing unit 62 includes the holding section 210 that stores the second container 21 positioned in the relay section 201. The holding section 210 is provided with a plurality of holding holes 211. With this configuration, the relay section 201 can be emptied by transferring the second container 21 from the relay section 201 to the holding section 210. Thus, the first processing unit 61 can transfer the second container 21 to the relay section 201 at an arbitrary timing.

When the plurality of holding holes 211 of the holding section 210 is full of the second containers 21, the second controller 62a transmits information indicating that "the holding section 210 is full" to the controller 64a. Then, the controller 64a transmits to the first controller 61a information indicating that "transfer of the second container 21 to the second processing unit 62 is stopped". Thus, the transfer of the second container 21 from the first processing unit 61 to the second processing unit 62 is temporarily stopped. When the measurement of the sample proceeds in the second processing unit 62, and there is a vacant holding hole 211 in the holding section 210, the second controller 62a transmits information indicating that "the holding section 210 can store the second container 21" to the controller 64a. Then, the controller 64a transmits to the first controller 61a information indicating that "transfer of the second container 21 to the second processing unit 62 is possible".

In the above case, the information regarding the holding section 210 is exchanged between the second processing unit 62 and the first processing unit 61 via the controller 64a. However, the information regarding the holding section 210 can be directly exchanged between the second controller 62a and the first controller 61a without the intervention of the controller 64a.

In step S103 in FIGS. 9A to 9C, the second controller 62a transmits the second signal indicating that the second container 21 has been received from the relay section 201 to the controller 64a, and also transmits the combined information of the sample ID of the sample contained in the received second container 21 and the measurement order to the controller 64a. The controller 64a stores the combination of each sample ID and the measurement order corresponding to each sample ID in the memory section 61b. However, the controller 64a is not particularly notified of the information indicating that the second container 21 is transported from the first processing unit 61 to the second processing unit 62 via the relay section 201. Therefore, the controller 64a does not recognize what kind of sample is being processed by the second processing unit 62. In view of this, the second controller 62a transmits to the controller 64a the combined information of the sample ID of the sample contained in the received second container 21 and the measurement order at the timing of transmitting the second signal to the controller 64a. Thus, the controller 64a can recognize that the sample to be measured is being supplied for the measurement without delay.

In the above steps S16 to S18, the controller 64a determines whether the order of the first measurement is set for the sample ID, and dispenses the sample and performs the first measurement on the sample by controlling the first controller 61a. These steps may be performed by the first controller 61a.

Specifically, in step S16, the first controller 61a determines whether the measurement order of the first measurement for the sample ID is set on the basis of the combined information of the sample ID and the measurement order acquired in steps S13 and S14. When the measurement order of the first measurement is set for the sample in step S16, the first controller 61a causes the dispensing section 30 to discharge the sample to the second container 21 in step S17. Then, the first controller 61a performs the first measurement based on the sample by the first measuring section 51.

In steps S19 and S20, the second controller 62a determines whether the measurement order of the second measurement for the sample ID is set on the basis of the combined information of the sample ID and the measurement order acquired in steps S13 and S14. When the measurement order of the second measurement is set for the sample in step S17, the first controller 61a causes the dispensing section 30 to discharge the sample to be subjected to the second measurement to the second container 21 in step S20.

Second Embodiment

Figure 10:
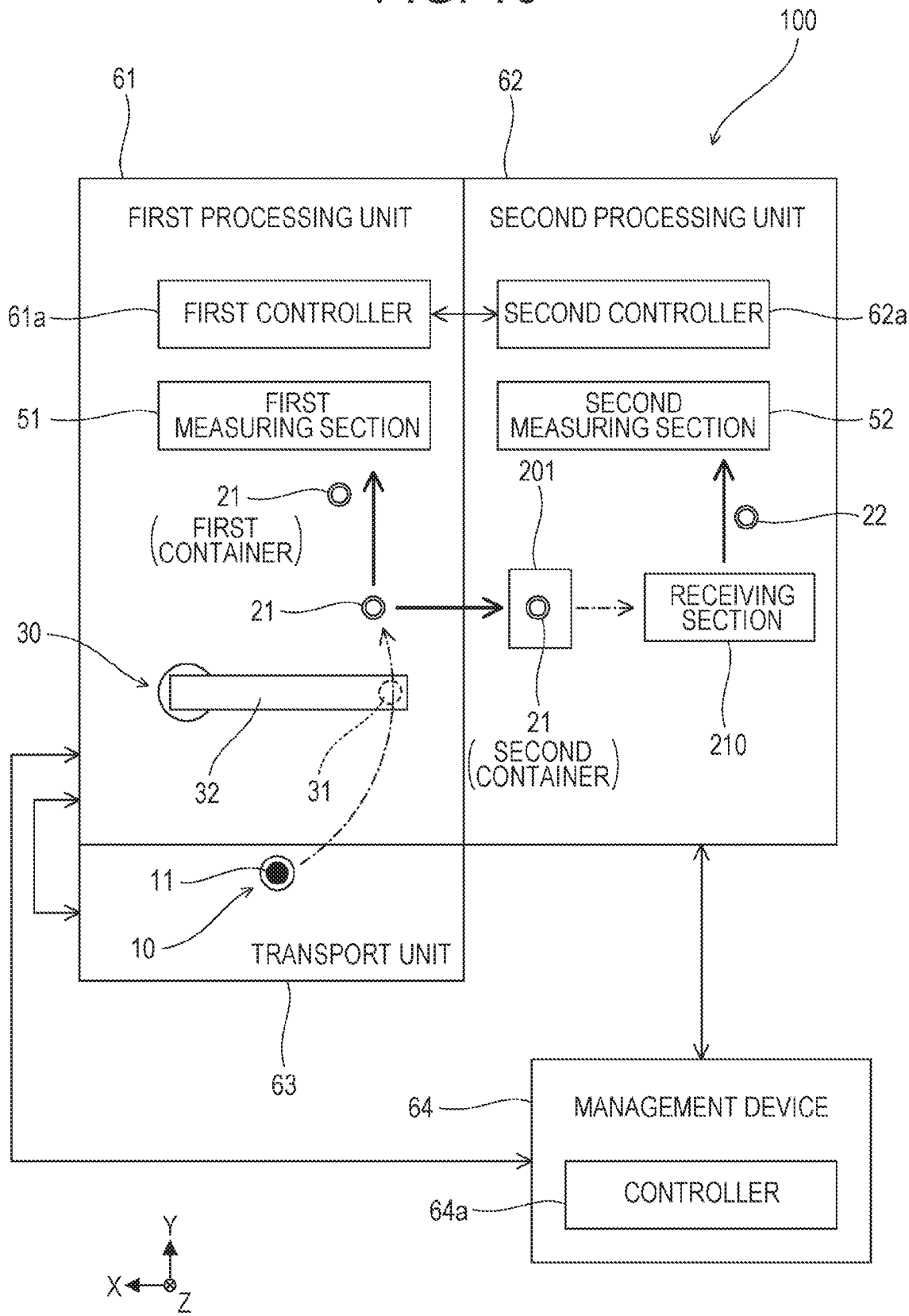
FIG. 10 is a diagram schematically showing a sample measurement device according to a second embodiment.

As shown in FIG. 10, a sample measurement device 100 according to the second embodiment transfers and receives the second container 21 between the first controller 61a and the second controller 62a via the relay section 201 without the intervention of the controller 64a of the management device 64.

A process of the sample measurement device 100 according to the second embodiment will be described with reference to FIGS. 8, 11A, and 11B. Steps S1 to S21 in the flowchart shown in FIG. 8 are the same as those in the first embodiment, and thus description thereof will be omitted.

Figure 11A:
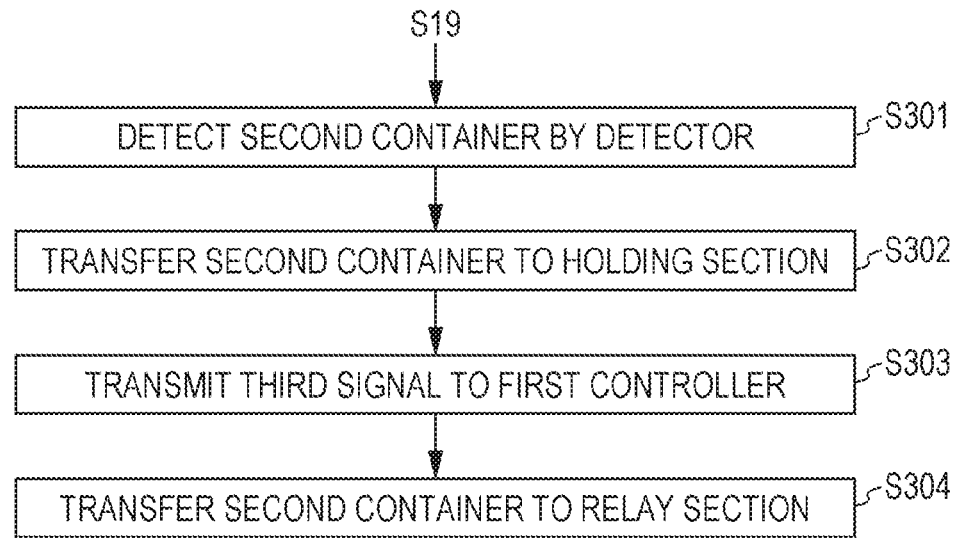
FIG. 11A is a flowchart showing a process involved with transfer and reception of a second container in a relay section in the sample measurement device according to the second embodiment.

As shown in FIG. 11A, when the controller 64a causes the first controller 61a to drive the dispensing section 30 to discharge the sample into the second container 21 in step S19 in FIG. 8, the processes similar to those in steps S101 and S102 in FIG. 9A are performed in steps S301 and S302.

In step S302, the reception of the second container 21 by the second processing unit 62 is completed, and therefore, the holding hole 201a of the relay section 201 is vacant in step S303. Therefore, the first processing unit 61 can position the second container 21 in the relay section 201. At this time, the second controller 62a transmits to the first controller 61a a third signal indicating that the second container 21 can be transferred to the relay section 201.

In step S304, when the third signal is transmitted from the second controller 62a, the first controller 61a drives the transfer section 142 at an arbitrary timing to transfer the second container 21 to the relay section 201.

Figure 11B:
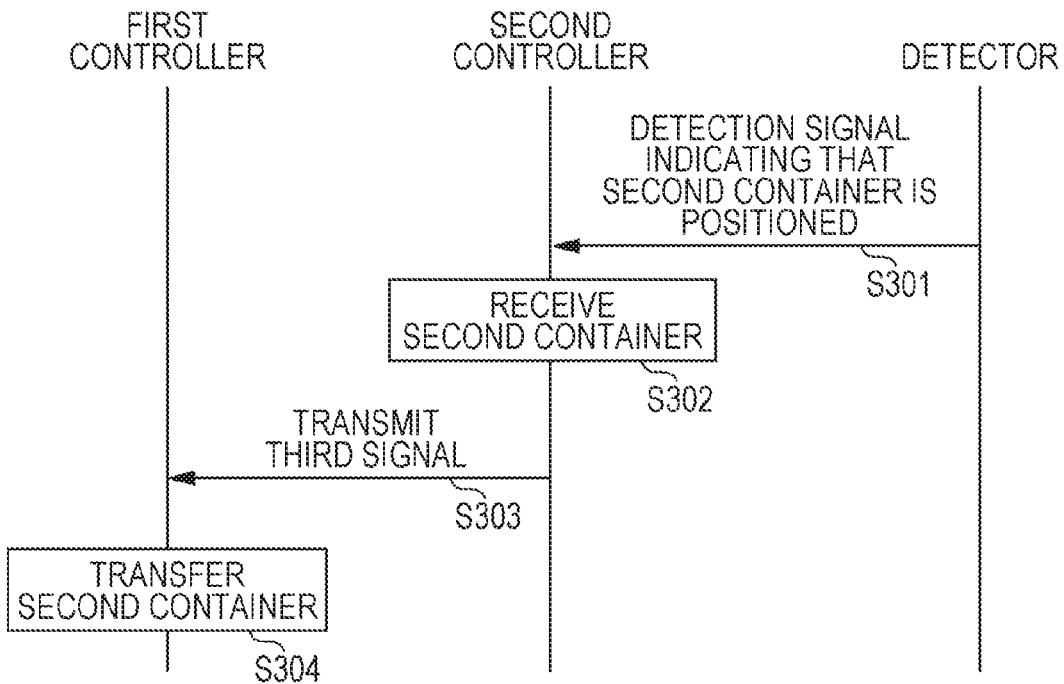
FIG. 11B is a sequence diagram indicating the process shown in FIG. 11A.

FIG. 11B is a sequence diagram showing the processes in the first processing unit 61 and the second processing unit 62 described with reference to FIG. 11A. As shown in FIG. 11B, when the detector 201b detects that the second container 21 has been positioned in the relay section 201, the light receiver 81 transmits a signal indicating this situation to the second controller 62a (S301). On the basis of the signal, the second controller 62a drives the transfer section 202 to receive the second container 21 from the relay section 201 and transfer the second container 21 to the holding section 210 (S302). Then, the third signal indicating that the second container 21 can be transferred to the relay section 201 is transmitted from the second controller 62a to the first controller 61a (S303). When receiving the third signal, the first controller 61a drives the transfer section 142 to transfer the second container 21 to the relay section 201 (S304).

In this way, the second container 21 is transferred from the first processing unit 61 to the second processing unit 62 via the relay section 201.

The sample measurement device 100 according to the second embodiment transfers and receives the second container 21 between the first controller 61a and the second controller 62a via the relay section 201 without the intervention of the controller 64a of the management device 64. Accordingly, the first processing unit 61 and the second processing unit 62 can more quickly transfer the second container 21 to the relay section 201 and receive the reaction container 21 from the relay section 201.

Third Embodiment

In the first and second embodiments, the detector 201b of the relay section 201, that is, the light receiver 81, is connected to only the second controller 62a. A sample measurement device 100 according to the third embodiment has a configuration in which the light receiver 81 is connected to both the first controller 61a and the second controller 62a.

Figure 12:
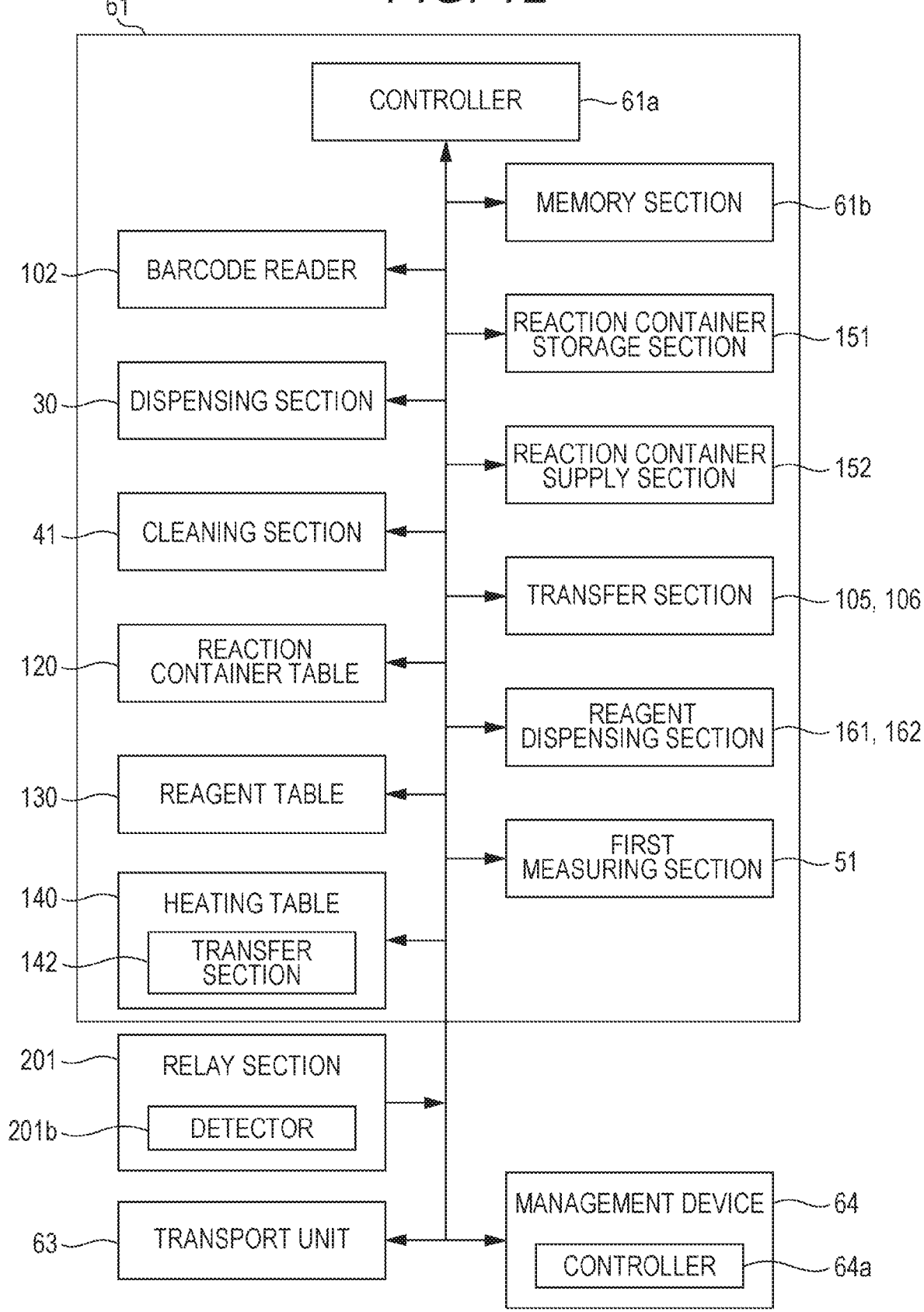
FIG. 12 is a diagram schematically showing a circuit configuration of a first processing unit according to a third embodiment.

As shown in FIG. 12, in the first processing unit 61, the first controller 61a is connected to the detector 201b of the relay section 201 in addition to the circuit configuration diagram shown in FIG. 6.

When the sample measurement device 100 is configured as described above, the signal of the light receiver 81 is output to both the first controller 61a and the second controller 62a. As described in the first embodiment, when the second container 21 is positioned in the relay section 201, the signal of the light receiver 81 falls to a low level, and when the second container 21 is transferred from the relay section 201, the signal of the light receiver 81 falls to a high level. Therefore, a signal indicating the presence or absence of the second container 21 in the relay section 201 is output from the detector 201b to the first controller 61a and the second controller 62a as a detection signal of the light receiver 81.

When a signal indicating the presence of the second container 21 is transmitted from the light receiver 81 to the second controller 62a, the second controller 62a drives the transfer section 202 to receive the second container 21 from the relay section 201. On the other hand, when a signal indicating that there is no second container 21 in the relay section 201 is transmitted from the light receiver 81 to the first controller 61a, the first controller 61a transfers the second container 21 to the relay section 201.

As described above, in the third embodiment, the second controller 62a does not need to transmit the second signal indicating that the second container 21 is received to the controller 64a, as it does in step S103, and the controller 64a does not need to transmit to the first controller 61a the first signal indicating that the second container 21 can be transferred, as it does in step S201, in FIGS. 9A to 9C in the first embodiment.

The second controller 62a does not need to transmit to the first controller 61a the first signal indicating that the second container 21 can be transferred, as it does in step S303 in FIGS. 11A and 11B in the second embodiment.

As described above, the first controller 61a of the first processing unit 61 and the second controller 62a of the second processing unit 62 can uniquely determine the presence or absence of the second container 21 in the relay section 201 on the basis of the signal from the detector 201b, that is, the light receiver 81. Further, they can uniquely perform the transferring operation and receiving operation of the second container 21 without receiving the notification from the counterpart processing unit. Therefore, the receiving operation and the transferring operation of the second container 21 can be performed under simpler control.

The detector 201b may not be configured to detect the presence or absence of the second container 21 by using light. For example, the detector 201b may be configured such that, when the second container 21 having a predetermined weight or more is stored in the relay section 201, a switch is turned on by the weight of the second container 21, and a signal indicating that the second container 21 is positioned in the relay section 201 is output to the second controller 62a. In this case, when the second processing unit 62 receives the second container 21 from the relay section 201, the switch is turned off, and a signal indicating that the second container 21 is not positioned in the relay section 201 is output to the first controller 61a. Thus, the first controller 61a knows that the relay section 201 is vacant, and can transfer the second container 21 to the relay section 201.

Other Modifications

In the first to third embodiments, the second processing unit 62 performs a measurement related to the immunological test. However, the second processing unit 62 may perform a measurement related to a test different from the immunological test. For example, the second processing unit 62 may perform a measurement related to a biochemical test. In this case, the second measuring section 52 performs a measurement related to the biochemical test. The second measuring section 52 has a configuration similar to that in the case of performing a measurement related to a blood coagulation test. That is, the second measuring section 52 in this case also irradiates the measurement sample with light from the light source part 411 and receives transmitted light or scattered light generated from the measurement sample by the light receiving part 412. Then, the second controller 62a generates measurement data used in an analysis related to the biochemical test on the basis of the electric signal transmitted from the light receiving part 412.

The controller 64a performs an analysis related to a biochemical test on the basis of the measurement data generated by the second processing unit 62. Specifically, the controller 64a analyzes the analysis items such as T-BIL, D-BIL, AST, ALT, ALP, LDH, γ-GTP, T-CHO, CRE, and CK.

The second processing unit 62 may perform a measurement related to a genetic test.

In the first to third embodiments, the first measurement and the second measurement are different from each other. However, they may be the same.

Even when two measurements are the same, the cycles in the respective measurements may differ. If the sample measurement device 100 is used in such a case, the two processing units can transfer the second container 21 to the relay section 201 and receive the second container 21 from the relay section 201 at an arbitrary timing without being affected by each other's operating statuses.

Figure 13:
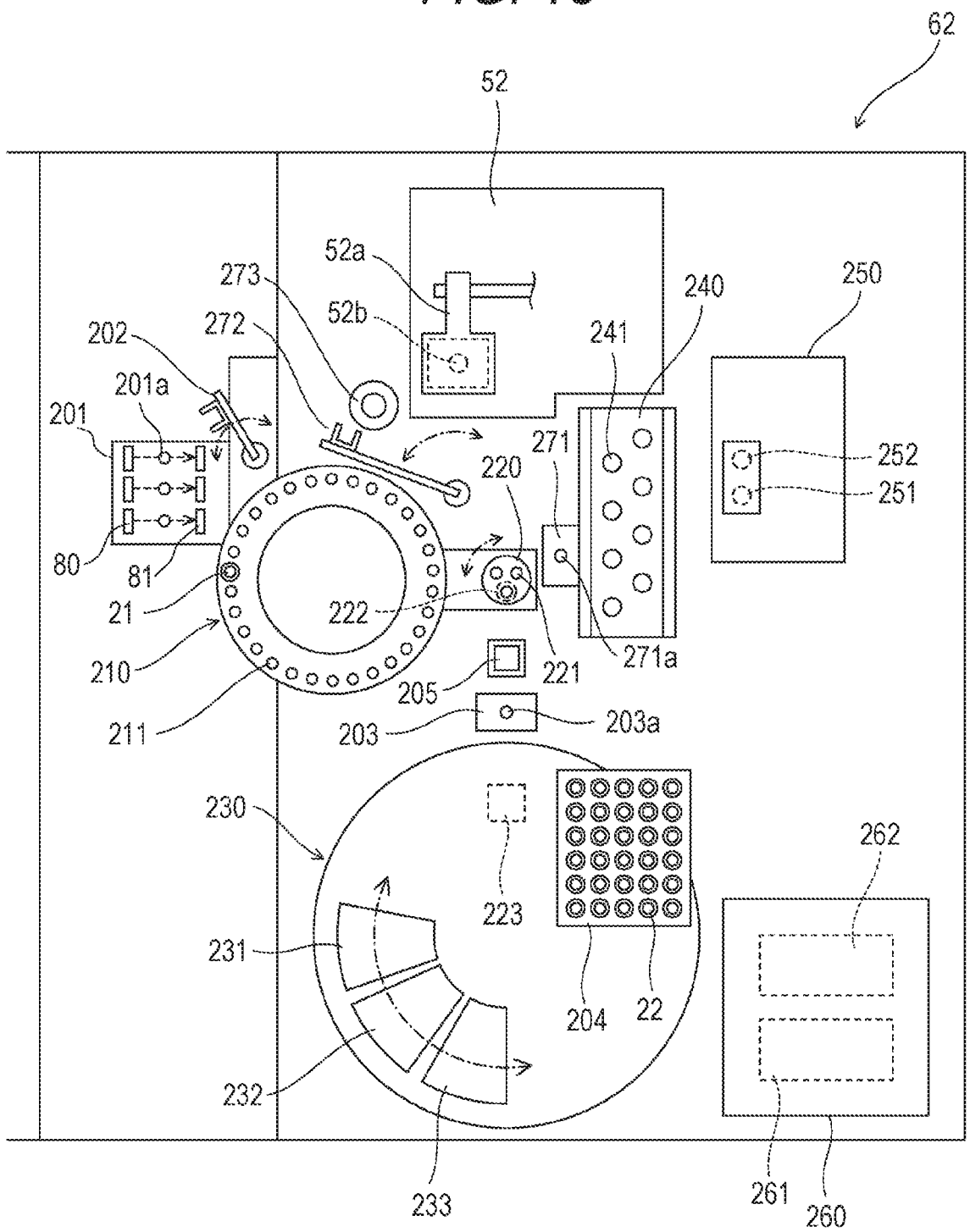
FIG. 13 is a view schematically showing a configuration of a second processing unit according to a modification.

Although the number of the holding holes 201a of the relay section 201 shown in FIG. 3 is one, a plurality of the holding holes 201a may be provided in the relay section 201 as shown in FIG. 13. In this case, the detector 201b is provided for each holding hole 201a.

For example, when the second processing unit 62 is performing the second measurement, and has not yet received the second container 21 from the relay section 201, the first processing unit 61 can transfer the second container 21 to the vacant holding hole 201a of the relay section 201. Therefore, the first processing unit 61 can transfer the second container 21 to the relay section 201 at an arbitrary timing of the first processing unit 61 without being affected by the operating status of the second processing unit 62.

In the first to third embodiments, the second container 21 positioned in the relay section 201 is transferred to the holding section 210, and then, is subjected to the second measurement. However, the second container 21 may be directly transferred to the second measuring section 52 from the relay section 201. In this case, the second container 21 is transferred to the second measuring section 52 without passing through the holding section 210, so that the second measurement is performed efficiently.

In the first to third embodiments, the sample contained in the sample container 10 is dispensed into the first container 21, and then, the sample contained in the sample container 10 is dispensed into the second container 21. However, after the sample is subjected to the first measurement, the sample contained in the first container 21 may be dispensed into the second container 21.

What is claimed is:

1. A sample measurement device comprising:
   a first processing unit comprising a first controller, a dispensing section, a first measuring section and a first holder, wherein the first measuring section is configured to perform a first measurement on a sample contained in a first container in a first cycle, and the first controller is configured to control the dispensing section and the first measuring section;
   a second processing unit comprising a second controller, a second measuring section and a second holder, wherein the second measuring section is configured to perform a second measurement on a sample contained in a second container in a second cycle different from the first cycle, and the second controller is configured to control the second measuring section;
   a relay section which is disposed between the first processing unit and the second processing unit, wherein the relay section has at least one holding hole for holding the second container and includes a detector that detects the second container held by the at least one holding hole, and the first controller and the second controller are independently connected to the detector; and
   a transport unit that is different from the relay section and that is configured to transport at least one sample container to a dispensing position of the dispensing section of the first processing unit;
   wherein the dispensing section is configured to dispense a sample contained in the at least one sample container positioned at the dispensing position into the first container and the second container in the first processing unit,
   wherein the first controller of the first processing unit is further configured to perform a transferring operation of transferring the second container to the relay section by the first holder, and the second controller of the second processing unit is further configured to perform a receiving operation of receiving the second container, from the relay section by the second holder, that has been transferred to the relay section by the first holder.

2. The sample measurement device according to claim 1, further comprising a management device comprising a third first-controller, wherein the management device is configured to communicate with the first processing unit and the second processing unit and the relay section,
   wherein the management device transmits, to the first processing unit, a first signal indicating that the second container is transferable to the relay section on the basis of a detection result of the detector, and the first processing unit executes the transferring operation when receiving the first signal.

3. The sample measurement device according to claim 2, wherein the second processing unit is configured such that, when the second container is detected in the relay section, the second processing unit executes the receiving operation and transmits, to the management device, a second signal indicating that the second processing unit receives the second container that has been positioned in the relay section, and the management device is configured to transmit the first signal to the first processing unit in response to receiving the second signal.

4. The sample measurement device according to claim 3, wherein the first processing unit includes a first transfer section that is configured to transfer the second container to the relay section, and the first controller further configured to control the first transfer section, the second processing unit includes a second transfer section that is configured to transfer the second container to a predetermined position from the relay section, and the second controller is further configured to control the second transfer section, the second controller is further configured to control the second transfer section to transfer the second container from the relay section to the predetermined position and transmit the second signal to the management device, when the second container is detected in the relay section, the management device is further configured to transmit the first signal to the first controller in response to receiving the second signal from the second controller, and the first controller is further configured to control the first transfer section to transfer the second container to the relay section in response to receiving the first signal from the management device.

5. The sample measurement device according to claim 1, wherein the relay section has a plurality of holding holes for holding the second container.

6. The sample measurement device according to claim 1, wherein the second processing unit includes a holding section configured to hold the second container transferred from the relay section.

7. The sample measurement device according to claim 1, wherein the first measurement is a measurement related to a blood coagulation test, and the second measurement is a measurement related to an immunological test.

8. The sample measurement device according to claim 1, wherein the dispensing section is configured to dispense the sample into the first container and the second container from one sample container.

9. The sample measurement device according to claim 1, wherein the dispensing section is configured to dispense the sample into the first container from one sample container and to dispense the sample into the second container from the first container.

10. The sample measurement device according to claim 1, wherein the relay section is arranged on the second processing unit side.

* * * * *

UNITED STATES PATENT AND TRADEMARK OFFICE
CERTIFICATE OF CORRECTION

| | |
|---|---|
| PATENT NO. | : 12,078,648 B2 |
| APPLICATION NO. | : 16/824198 |
| DATED | : September 3, 2024 |
| INVENTOR(S) | : Masaki Shiba et al. |

Page 1 of 1

It is certified that error appears in the above-identified patent and that said Letters Patent is hereby corrected as shown below:

In the Claims

Column 26, Claim 2, Line 63, delete "first-".

Column 27, Claim 4, Line 21, between "controller" and "further", insert --is--.

Signed and Sealed this
Thirty-first Day of December, 2024

Derrick Brent
*Acting Director of the United States Patent and Trademark Office*